US010573817B2

(12) United States Patent
Pillow et al.

(10) Patent No.: US 10,573,817 B2
(45) Date of Patent: Feb. 25, 2020

(54) HOLE TRANSPORTING COMPOUNDS AND COMPOSITIONS

(71) Applicants: Cambridge Display Technology Limited, Godmanchester (GB); Sumitomo Chemical Company Limited, Tokyo (JP)

(72) Inventors: Jonathan Pillow, Godmanchester (GB); Martin Humphries, Godmanchester (GB); Ruth Pegington, Godmanchester (GB); Florence Bourcet, Godmanchester (GB); Yonek Hleba, Godmanchester (GB); Thomas Kugler, Cambridge (GB); Sheena Zuberi, Godmanchester (GB)

(73) Assignees: Cambridge Display Technology Limited, Godmanchester (GB); Sumitomo Chemical Company Limited, Tokyo (JP)

( * ) Notice: Subject to any disclaimer, the term of this patent is extended or adjusted under 35 U.S.C. 154(b) by 331 days.

(21) Appl. No.: 15/325,022

(22) PCT Filed: Jul. 8, 2015

(86) PCT No.: PCT/GB2015/051981
§ 371 (c)(1),
(2) Date: Jan. 9, 2017

(87) PCT Pub. No.: WO2016/005749
PCT Pub. Date: Jan. 14, 2016

(65) Prior Publication Data
US 2017/0207393 A1    Jul. 20, 2017

(30) Foreign Application Priority Data
Jul. 9, 2014    (GB) .................................. 1412213.9

(51) Int. Cl.
*H01L 51/00* (2006.01)
*C08G 61/12* (2006.01)
(Continued)

(52) U.S. Cl.
CPC ........ *H01L 51/0039* (2013.01); *C07C 13/567* (2013.01); *C08G 61/12* (2013.01);
(Continued)

(58) Field of Classification Search
CPC .................................................. H01L 51/0039
See application file for complete search history.

(56) References Cited

U.S. PATENT DOCUMENTS

2001/0053842 A1* 12/2001 Woo .................... C07C 17/2637
528/397
2014/0151677 A1* 6/2014 Shiomi ................ C07D 209/86
257/40
2014/0163175 A1* 6/2014 Okada ...................... G02B 1/04
525/326.5

FOREIGN PATENT DOCUMENTS

GB    1412213.9    5/2015
JP    2001-520284 A    10/2001
(Continued)

OTHER PUBLICATIONS

Combined Search and Examination Report dated May 19, 2015 for Application No. GB1412213.9.
(Continued)

*Primary Examiner* — Robert A Vetere
(74) *Attorney, Agent, or Firm* — Wolf, Greenfield & Sacks, P.C.

(57) ABSTRACT

A composition comprising a first material substituted with at least one group of formula (I) and a second material substituted with at least one group selected from groups of formulae (IIa) and (IIb): wherein: $Sp^1$ and $Sp^2$ are spacer
(Continued)

groups; NB independently in each occurrence is a norbornene group that may be unsubstituted or substituted with one or more substituents; n1 and n2 are 0 or 1; m1 is 1 if n1 is 0 and m1 is at least 1 if n1 is 1; m2 is 1 if n2 is 0 and m2 is at least 1 if n2 is 1; $Ar^1$ represents an aryl or heteroaryl group; $R^1$ independently in each occurrence is H or a substituent; and * represents a point of attachment to the first or second material. The composition may be used to form a layer of an organic electronic device, for example the hole-transporting layer of an organic light-emitting device.

20 Claims, 5 Drawing Sheets

(51) Int. Cl.
    *C09K 11/06* (2006.01)
    *C07C 13/567* (2006.01)
    *H01L 51/50* (2006.01)

(52) U.S. Cl.
    CPC ............ *C08G 61/122* (2013.01); *C09K 11/06* (2013.01); *H01L 51/0003* (2013.01); *H01L 51/004* (2013.01); *H01L 51/0035* (2013.01); *H01L 51/0043* (2013.01); *H01L 51/0058* (2013.01); *C07C 2602/42* (2017.05); *C07C 2603/18* (2017.05); *C08G 2261/124* (2013.01); *C08G 2261/148* (2013.01); *C08G 2261/149* (2013.01); *C08G 2261/1412* (2013.01); *C08G 2261/1526* (2013.01); *C08G 2261/18* (2013.01); *C08G 2261/228* (2013.01); *C08G 2261/312* (2013.01); *C08G 2261/314* (2013.01); *C08G 2261/3142* (2013.01); *C08G 2261/3162* (2013.01); *C08G 2261/95* (2013.01); *H01L 51/5056* (2013.01)

(56) References Cited

FOREIGN PATENT DOCUMENTS

| | | |
|---|---|---|
| JP | 2012/111719 A | 6/2012 |
| JP | 2013-023491 A | 2/2013 |
| JP | 2013-028758 A | 2/2013 |
| JP | 2013-129716 A | 7/2013 |
| JP | 2014-013840 A | 1/2014 |
| KR | 10-2009-0093144 A | 9/2009 |
| WO | WO 2004/073018 A2 | 8/2004 |
| WO | WO 2009/080799 A2 | 7/2009 |
| WO | WO 2013/005026 A2 | 1/2013 |
| WO | WO 2013/018817 A1 | 2/2013 |
| WO | PCT/GB2015/051981 | 9/2015 |

OTHER PUBLICATIONS

International Search Report and Written Opinion dated Sep. 9, 2015 for Application No. PCT/GB2015/051981.

* cited by examiner

HOLE TRANSPORTING COMPOUNDS AND COMPOSITIONS

RELATED APPLICATIONS

This application is a national stage filing under 35 U.S.C. § 371 of international PCT application, PCT/GB2015/051981, filed Jul. 8, 2015, which claims priority to United Kingdom patent application, GB 1412213.9, filed Jul. 9, 2014, each of which is incorporated herein by reference in its entirety.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

A light emitting layer may comprise a semiconducting host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton).

Phosphorescent dopants are also known (that is, a light-emitting dopant in which light is emitted via decay of a triplet exciton).

A hole-transporting layer may be provided between the anode and the light-emitting layer.

"Synthesis and Application of Photolithographically Patternable Deep Blue Emitting Poly(3,6-Dimethoxy-9,9-dialkylsilafluorene)s" Applied Materials & Interfaces (2014), 6(1), 83-93 discloses formation of a patterned light-emitting layer by depositing a blue-emitting poly(silafluorene) and reacting norbornene substituents of the polymer by photolithography.

KR 2009/093144 discloses polymerisation of a norbornene monomer substituted with a triarylamine group.

Chemistry of Materials (2007), 19(23), 5602-5608 discloses norbornene-based copolymers with iridium complexes and bis (carbazolyl) fluorene groups in their sidechains and their use in light-emitting diodes.

WO 2013/005026 discloses hole-transporting polymers substituted with benzocyclobutene groups. Use of these polymers as the hole-transporting layer of an OLED is disclosed. The benzocyclobutene groups are crosslinked to render the layer insoluble. The benzocyclobutene groups may be reacted with each other or may be reacted with a double bond group.

It is an object of the invention to improve performance of organic electronic devices, in particular organic light-emitting devices, in which one or more layers of the device is formed by deposition of a semiconducting layer of the device by a solution deposition method.

SUMMARY OF THE INVENTION

In a first aspect the invention provides a composition comprising a first material substituted with at least one group of formula (I) and a second material substituted with at least one group selected from groups of formulae (IIa) and (IIb):

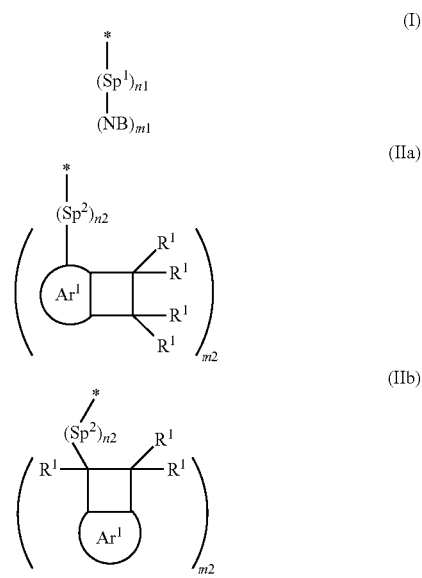

wherein:
Sp$^1$ represents a first spacer group;
NB independently in each occurrence is a norbornene group that may be unsubstituted or substituted with one or more substituents;
n1 is 0 or 1;
m1 is 1 if n1 is 0 and m1 is at least 1 if n1 is 1;
Sp$^2$ represents a second spacer group;
n2 is 0 or 1;
m2 is 1 if n2 is 0 and m2 is at least 1 if n2 is 1;
Ar$^1$ independently in each occurrence represents an aryl or heteroaryl group that may be unsubstituted or substituted with one or more substituents;
R$^1$ independently in each occurrence is H or a substituent; and
\* represents a point of attachment to the first or second material.

In a second aspect, the invention provides a method of forming a layer of an organic electronic device comprising the step of reacting a composition according to the first aspect.

In a third aspect the invention provides a method of forming an organic light-emitting device, the method comprising the steps of forming a hole-transporting layer over an anode; forming a light-emitting layer on the hole-transporting layer; and forming a cathode over the light-emitting layer, wherein the step of forming the hole-transporting layer comprises depositing a first material substituted with at least one group of formula (I) hole-transporting layer over the anode and crosslinking the group of formula (I). The first material of this third aspect may be as described anywhere herein, and may be deposited and crosslinked by any deposition and crosslinking method described herein. The hole-transporting layer may be formed by forming and crosslinking a layer in which the first material is the only crosslinkable material, in which case the layer may consist essentially of the first material. The hole-transporting layer may be formed by forming and crosslinking a layer comprising both the first material and second material wherein the second material is as described anywhere herein.

In a fourth aspect the invention provides a method of forming a layer of an organic electronic device, the method comprising the steps of forming a layer comprising the first material and crosslinking the first layer by thermal treatment. Optionally, the organic electronic device is an organic light-emitting device. The first material of this fourth aspect may be as described anywhere herein, and may be deposited and thermally crosslinked by any deposition and thermal crosslinking method described herein. The layer may be formed by forming and thermally crosslinking a layer in which the first material is the only crosslinkable material, in which case the layer may consist essentially of the first material. The layer may be formed by forming and thermally crosslinking a layer comprising both the first material and second material wherein the second material is as described anywhere herein.

In a fifth aspect the invention provides a non-polymeric compound comprising a core substituted with one or more groups of formula (I) wherein the one or more groups of formula (I) are bound to an aromatic group of the core. The core may be any core group comprising one or more aromatic groups described herein.

In a sixth aspect the invention provides a polymer comprising a repeat unit substituted with one or more groups of formula (I) wherein the one or more groups of formula (I) are bound to one or more aromatic groups of the repeat unit. The repeat unit may be any repeat unit described herein comprising one or more aromatic groups.

The non-polymeric compound of the fifth aspect and the polymer of the sixth aspect may be reacted to form a layer of an organic electronic device as described anywhere herein, for example the hole-transporting layer of an organic light-emitting device.

DESCRIPTION OF THE DRAWINGS

The invention will now be described in more detail with reference to the drawings in which.

DETAILED DESCRIPTION OF THE INVENTION

Figure 1:
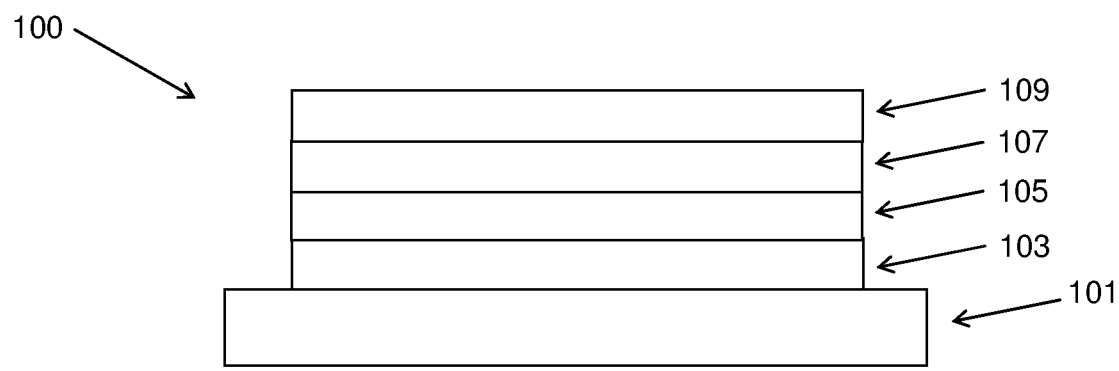
FIG. 1 illustrates schematically an OLED according to an embodiment of the invention.

FIG. 1, which is not drawn to any scale, illustrates an OLED 100 according to an embodiment of the invention comprising an anode 103, a cathode 109, a light-emitting layer 107 between the anode and cathode and a hole-transporting layer 105 between the anode and the light-emitting layer. The device 100 is supported on a substrate 101, for example a glass or plastic substrate.

Light-emitting layer 107 may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display. If the light-emitting layer 107 is patterned then hole-transporting layer 105 may be patterned in the same way as the light-emitting layer, or a patterned light-emitting layer 107 may be formed on an unpatterned hole-transporting layer 105.

Hole-transporting layer 105 contains a hole-transporting material. The hole-transporting layer is formed by reacting a first material containing a group of formula (I) with a second material containing a group of formula (IIa) or (IIb).

To form the hole-transporting layer, the first and second materials are deposited over the anode. The group of formula (I) is then reacted with the group of formula (IIa) or (IIb). A light-emitting layer 107 is then formed on the hole-transporting layer 105.

Preferably, the light-emitting layer is formed by depositing a formulation of the material or materials of the light-emitting layer dissolved or dispersed in a solvent or solvent mixture followed by evaporation of the solvent or solvents. Preferably, hole-transporting layer 105 is rendered insoluble by the reaction of the group of formula (I) with the group of formula (IIa) or (IIb) such that little or none of the hole-transporting layer is dissolved by the solvent or solvents used to form the light-emitting layer, and such that there is little or no intermixing between the materials of the hole-transporting layer and the material or materials of the light-emitting layer. Preferably, the first material and second material react to form a crosslinked hole-transporting layer.

In another embodiment, the first material is the only crosslinkable material used to form the hole-transporting layer 105, in which case the hole-transporting layer is formed by reaction between groups of formula (I). One or more further layers may be provided between the anode 103 and cathode 109. Further layers may be selected from one or more further light emitting layers, hole-injection layers, hole-transporting layers, electron transporting layers, hole blocking layers and electron blocking layers.

Preferred device structures include:
Anode/Hole transporting layer/Light-emitting layer/Cathode
Anode/Hole-injection layer/Hole-transporting layer/Light-emitting layer/Cathode
Anode/Hole-injection layer/Hole-transporting layer/Light-emitting layer/Electron-transporting layer/Cathode.

Preferably, both a hole injection layer and hole-transporting layer are present.

Light-emitting materials of the OLED 100 may be fluorescent materials, phosphorescent materials or a mixture of fluorescent and phosphorescent materials. Light-emitting materials may be selected from polymeric and non-polymeric light-emitting materials. Exemplary light-emitting polymers are conjugated polymers, for example polyphenylenes and polyfluorenes examples of which are described in Bernius, M. T., Inbasekaran, M., O'Brien, J. and Wu, W., Progress with Light-Emitting Polymers. Adv. Mater., 12: 1737-1750, 2000, the contents of which are incorporated herein by reference. Light-emitting layer 107 may comprise a host material and a fluorescent or phosphorescent light-emitting dopant. Exemplary phosphorescent dopants are row 2 or row 3 transition metal complexes, for example complexes of ruthenium, rhodium, palladium, rhenium, osmium, iridium, platinum or gold.

The OLED may be a white-emitting OLED. A white-emitting OLED may contain a single, white-emitting layer or may contain two or more layers that emit different colours which, in combination, produce white light. White light may be produced from a combination of red, green and blue light-emitting materials provided in a single light-emitting layer or distributed within two or more light-emitting layers. In a preferred arrangement, the device has a light-emitting layer comprising a red light-emitting material and a light-emitting layer comprising green and blue light-emitting materials. Preferably, all light-emitting materials of a white-emitting OLED are phosphorescent.

The light emitted from a white-emitting OLED may have CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-4500K.

A blue light emitting material may have a photoluminescent spectrum with a peak in the range of 420-490 nm, more preferably 420-480 nm.

A green light emitting material may have a photoluminescent spectrum with a peak in the range of more than 490 nm up to 580 nm, optionally more than 490 nm up to 540 nm.

A red light emitting material may optionally have a peak in its photoluminescent spectrum of more than 580 nm up to 630 nm, optionally 585-625 nm.

Light-emitting layer 107 may be the only emissive layer of the device, or light may be emitted from one or more further layers of the device. A light-emitting dopant may be provided in hole-transporting layer 105 such that hole-transporting layer 105 and light-emitting layer 107 together emit white light when the device is in use.

In another embodiment (not shown) light-emitting layer 107 may be formed by reaction of a composition as described herein, in which case hole-transporting layer 105 may or may not be present. Light-emitting layer 107 of this embodiment may be the only layer between the anode and the cathode, or one or more further layers, for example as described above, may be provided between the anode and cathode.

In another embodiment (not shown), an electron-transporting layer or electron injecting layer may be provided between the light-emitting layer 107 and the cathode 109 wherein the electron-transporting or electron-injecting layer is formed by crosslinking a first material. The first material may be reacted with itself, or the electron-transporting or electron-injecting layer may be formed by reacting a composition comprising a first material and a second material. The device of this embodiment may contain the light-emitting layer 107 and the electron-transporting or electron-injecting layer only between the anode and cathode, or one or more further layers, for example as described above, may be provided between the anode and cathode.

Formula (I)

The norbornene group NB of formula (I) may be unsubstituted or may be substituted with one or more substituents.

$Sp^1$ may be a group of formula $—(R^{11})_t—$ wherein t is at least 1, optionally 1, 2, 3, 4 or 5 and each $R^{11}$ is independently selected from the group consisting of:

$C_{1-20}$ alkyl wherein one or more non-adjacent C atoms of the alkyl may be replaced with, O, S, $SiR^2_2$ wherein $R^2$ in each occurrence is independently a substituent or an aryl or heteroaryl group that may be unsubstituted or substituted with one or more substituents; and aryl or heteroaryl that may be unsubstituted or substituted with one or more substituents.

$Sp^1$ may be substituted with one or more norbornene groups NB. $Sp^1$ may be a branched group having at least two branches wherein at least two of the branches are substituted with a norbornene group NB.

$R^2$ independently in each occurrence may be a hydrocarbyl group, optionally a hydrocarbyl group selected from $C_{1-20}$ alkyl and phenyl that may be unsubstituted or substituted with one or more $C_{1-10}$ alkyl groups.

Aryl or heteroaryl groups $Sp^1$ or forming part of $Sp^1$ are preferably selected from $C_{6-20}$ aryl groups that may be unsubstituted or substituted with one or more substituents, preferably phenyl that may be unsubstituted or substituted with one or more substituents, optionally one or more $C_{1-10}$ alkyl groups.

Exemplary spacer groups $Sp^1$ include $C_{1-20}$ alkyl, $C_{1-20}$ alkoxy, phenyl, phenyl-$C_{1-20}$ alkyl; phenyl-$C_{1-20}$ alkoxy; groups containing polyether units for example a spacer of formula $—(C_2H_5O)_p—$ or -phenyl-$(OC_2H_5)_p—$ wherein p is at least 2, optionally 2-10 and phenyl is unsubstituted or substituted with one or more substituents, optionally one or more $C_{1-20}$ alkyl groups; $—(R^{10})_q—Si(R^2)_2—(R^1)_q—$ wherein $R^2$ is as described above; $R^{10}$ in each occurrence is $C_{1-20}$ hydrocarbyl; and q in each occurrence is 0 or 1. $R^{10}$ in each occurrence may independently be selected from $C_{1-20}$ alkyl and phenyl that may be unsubstituted or substituted with one or more $C_{1-10}$ alkyl groups.

Formulae (IIa) and (IIb)

$R^1$ in each occurrence is independently H or a substituent.

In an embodiment, each $R^1$ is H.

A substituent $R^1$ may increase reactivity of the group of formula (IIa) or (IIb).

In another embodiment, at least one $R^1$ is a substituent (i.e., not H). Optionally according to this embodiment, only one $R^1$ is a substituent. Exemplary substituents $R^1$ may be selected from the group consisting of:

$C_{1-20}$ alkyl;
$C_{1-20}$ alkoxy;
tri(hydrocarbyl)silyl;

aryl or heteroaryl that may be unsubstituted or substituted with one or more substituents, optionally phenyl that may be unsubstituted or substituted with one or more $C_{1-10}$ alkyl or $C_{1-10}$ alkoxy groups.

Optionally, hydrocarbyl of tri(hydrocarbyl)silyl may be selected from the group consisting of $C_{1-20}$ alkyl and phenyl that may be unsubstituted or substituted with one or more $C_{1-10}$ alkyl groups.

Substituents $R^1$, where present, are preferably selected from $C_{1-10}$ alkyl. $R^1$ may be a linear, branched or cyclic alkyl group.

Optionally, $Ar^1$ is an aryl group, optionally a $C_{6-20}$ aryl group, that may be unsubstituted or substituted with one or more substituents.

Preferably, $Ar^1$ is phenyl that may be unsubstituted or substituted with one or more substituents, optionally one or more $C_{1-10}$ alkyl groups.

$Sp^2$ may independently in each occurrence be selected from groups $Sp^1$ described above.

$Sp^2$ may be substituted with one or more (hetero)arylcyclobutene groups. $Sp^2$ may be a branched group having at least two branches wherein at least two of the branches are substituted with a (hetero)arylcyclobutene group.

First and Second Materials

The first material substituted with a group of formula (I) and the second material substituted with a group of formula (IIa) or (IIb) may each independently be a non-polymeric material or a polymer comprising a repeat unit substituted with a group of formula (I), (IIa) or (IIb).

"Non-polymeric material" as used herein means a compound having a polydispersity of 1, and includes dendrimeric or oligomeric compounds having a polydispersity of 1. Oligomers include, without limitation, a dimer, a trimer, a tetramer or a pentamer. Preferably, non-polymeric materials have a molecular weight of less than about 5,000 Daltons.

A non-polymeric first material may have formula (IIIa):

(IIIa)

wherein Core1 is a non-polymeric first core group; $Sp^1$ is a first spacer group; n1 is 0 or 1; NB is a norbornene group that may be unsubstituted or substituted with one or more substituents; if n1 is 0 then m1 is 1; if n1 is 1 then m1 is at least 1, optionally 1, 2 or 3; and p1 is at least 1, optionally 1, 2, 3 or 4.

The non-polymeric first material may have formula (IIIb):

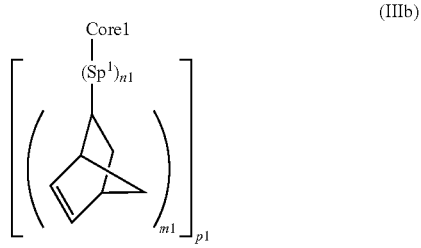

(IIIb)

A polymeric first material may comprise a repeat unit of formula (IIIc):

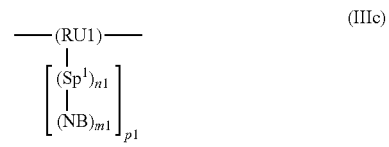

(IIIc)

wherein RU1 is a first repeat unit. A repeat unit of formula (IIIc) may form 0.5-25 mol % of the repeat units of the polymer, optionally 1-20 mol % of the repeat units.

The repeat unit of formula (IIIc) may be a repeat unit of formula (IIId)

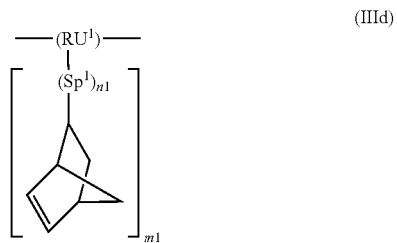

(IIId)

The norbornene group NB of formulae (IIIa) and (IIIc) may be bound to Core1 or to RU1, either directly or through $Sp^1$, through any position of the norbornene group.

The norbornene group of formulae (I), (IIIa), (IIIb), (IIIc) or (IIId) may be unsubstituted as shown in formulae (IIIb) and (IIId), or substituted with one or more substituents. Exemplary substituents are $C_{1-20}$ alkyl wherein one or more non-adjacent C atoms may be replaced with O, S, S—O, C=O or COO; aromatic groups, optionally phenyl, that may be unsubstituted or substituted with one or more substituents; heteroaromatic groups that may be unsubstituted or substituted with one or more substituents; nitrile; and nitro. $C_{1-20}$ alkyl groups may be linear, branched or cyclic alkyl groups. Substituents of aromatic or heteroaromatic groups, where present, may be selected from $C_{1-20}$ alkyl.

A non-polymeric second material may have formula (IVa) or (IVb):

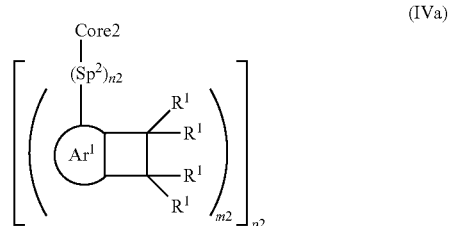

(IVa)

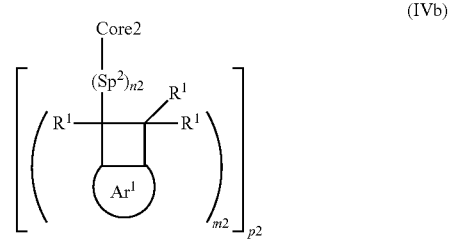

(IVb)

wherein Core2 is a non-polymeric second core group; $Sp^2$ is a second spacer group; $Ar^1$ is an aryl or heteroaryl group that may be unsubstituted or substituted with one or more substituents; $R^1$ in each occurrence is independently H or a substituent; n2 is 0 or 1; if n2 is 0 then m2 is 1; if n2 is 1 then m2 is at least 1, optionally 1, 2 or 3; and p2 is at least 1, optionally 1, 2, 3 or 4.

In another embodiment, a non-polymeric second material may be substituted with one or more groups of formula (IIa) and one or more groups of formula (IIb).

A polymeric second material may comprise a repeat unit of formula (IVc) or (IVd):

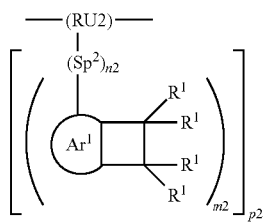
(IVc)

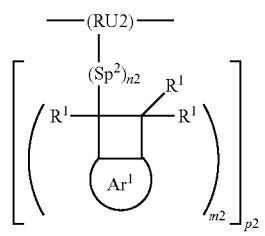
(IVd)

wherein RU2 is a second repeat unit.

In another embodiment, a second repeat unit may be substituted with one or more groups of formula (IIa) and one or more groups of formula (IIb).

$Ar^1$ of formulae (IVa) and (IVc) may be bound to Core2 or RU2, either directly or through $Sp^2$, through any position of $Ar^1$. Preferably, Ar1 is not bound through a ring atom adjacent to an atom of the benzocyclobutene ring.

A repeat unit substituted with one or more groups of formula (IIa) or (IIb), for example a repeat unit of formula (IVc) or (IVd), may form 0.5-25 mol % of the repeat units of the polymer, optionally 1-20 mol % of the repeat units.

A non-polymeric compound may contain at least one group of formula (I) (p1 is at least 1) and at least one group of formula (IIa) or (IIb) (p2 is at least 1), for example a compound of formula (XI) wherein Core3 is a non-polymeric third core group that may be selected from any core group described herein with reference to Core1 or Core2:

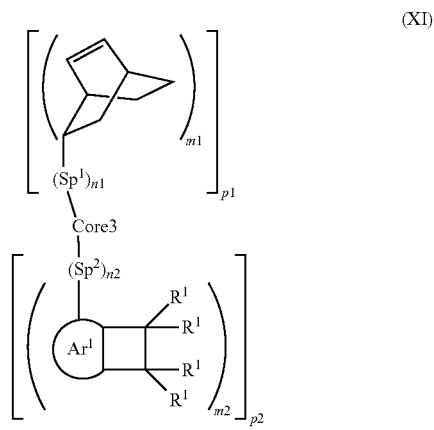
(XI)

It will therefore be appreciated that a composition as described herein may be a single non-polymeric compound substituted with least one group of formula (I) and at least one group of formula (IIa) or (IIb). In this case, the first material and second material are the same core material to which the group or groups of formula (I) and the group or groups of formula (IIa) or (IIb) are substituted.

The present inventors have found that groups of formula (I) react readily with groups of formula (IIa) or (IIb) in a Diels-Alder type reaction. Without wishing to be bound by any theory, it is believed that the ring strain of the norbornene group of formula (I) makes this group more reactive than a double bond group such as a double bond group in a chain. In the case where the first and second materials are reacted to form a crosslinked layer, a highly crosslinked layer may be formed. Compositions as described herein may be reacted by thermal treatment and/or by irradiation, for example UV irradiation. Preferably, the compositions are reacted by thermal treatment. Preferably, thermal treatment is at a temperature of less than 180° C., more preferable less than 160° C. Thermal treatment may be at a temperature of at least 130° C., optionally at least 140° C.

If the first material is a non-polymeric material having only one norbornene group (m1 and p1 are each 1) and second material is a non-polymeric having only one (hetero) arylcyclobutene group (m2 and p2 are each 1) then these materials may be reacted to give a Diels-Alder adduct as illustrated in Scheme 1.

Scheme 1

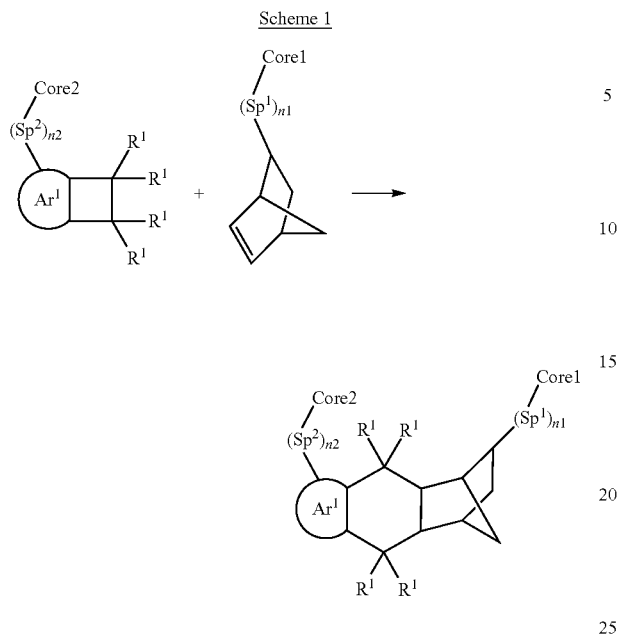

If the first non-polymeric material is substituted with two groups of formula (I), for example if m1=1 and p1=2, and if the second non-polymeric material is substituted with two groups of formula (IIa) or (IIb), for example if m2=1 and p2=2, then the first and second materials may react to form a linear polymer having the following repeating structure:

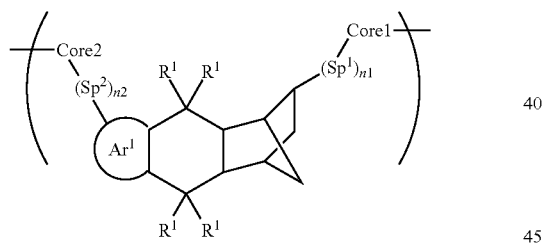

If the first non-polymeric material contains more than two norbornene groups and/or if the second non-polymeric material is substituted with more than two (hetero)arylcyclobutene groups then the first and second materials may react to form a crosslinked polymer.

If at least one of the first and second materials is a repeat unit of a polymer then the reaction may be a crosslinking reaction.

Scheme 2 illustrates a crosslinking reaction between two chains of a polymer comprising a repeat unit of formula (IIId) and a non-polymeric compound of formula (IVa) wherein m2 is 1 and p2 is 2, although it will be appreciated that m2 may be greater than 1 and/or p2 may be greater than 2, for example 3 or 4:

Scheme 2

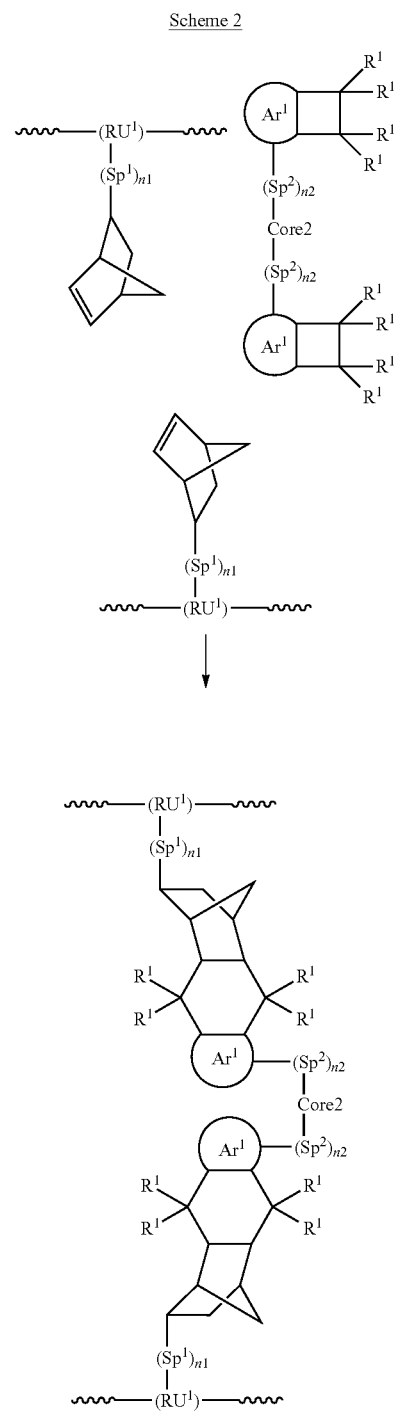

In another embodiment, a non-polymeric compound of formula (IIIa) wherein p1 is 2 or more and/or m1 is 2 or more is reacted with a polymer comprising repeat units of formula (IVc) or (IVd).

In another embodiment, the non-polymeric compound of formula (IVa) of Scheme 2 is replaced with a non-polymeric compound of formula (IVb).

Scheme 3 illustrates a crosslinking reaction between a polymer comprising repeat units of formula (IIIc) and a polymer comprising repeat units of formula (IVc):

Scheme 3

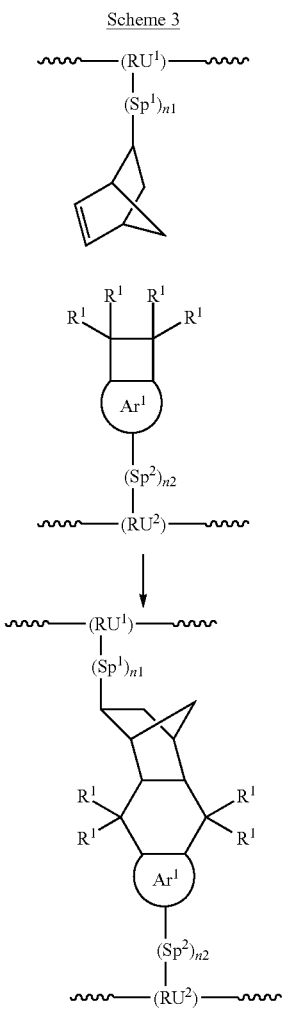

It will be appreciated that the polymer comprising repeat units of formula (IVc) of Scheme 3 may be replaced by a polymer comprising repeat units of formula (IVd).

A single polymer may contain both repeat units of formula (IIIc) and repeat units of formula (IVc) or (IVd), in which case the first and second materials are repeat units of the same polymer and the crosslinking reaction may be between chains of that polymer. It will therefore be appreciated that a composition as described herein may be a single polymer comprising both repeat units of formula (IIIc) and repeat units of formula (IVc) or (IVd). One or more further crosslinking materials may be present in addition to the polymer, for example one or more non-polymeric or polymeric crosslinking materials carrying one or more groups of formula (I), (IIa) or (IIb).

Core Groups

Core1 of a non-polymeric first material may be substituted only with one or more groups of formula (I) or may be substituted with one or more further substituents.

Core2 of a non-polymeric second material may be substituted only with one or more groups selected from formulae (IIa) or (IIb) or may be substituted with one or more further substituents.

Exemplary further substituents include $C_{1-40}$ hydrocarbyl groups, for example $C_{1-20}$ alkyl, unsubstituted phenyl and phenyl substituted with one or more $C_{1-20}$ alkyl groups.

Core1 and Core2 may be selected according to the function of the layer that they are to be present in. Optionally, Core1 and Core2 are each independently selected from hole-transporting groups, electron-transporting groups and light-emitting groups.

Preferably, Core1 and Core2 comprise at least one aromatic or heteroaromatic group, more preferably at least one aromatic group. Exemplary Core1 and Core2 groups include arylene groups, for example benzene and fluorene, and amine groups.

A first non-polymeric compound or second non-polymeric compound may have formula (V):

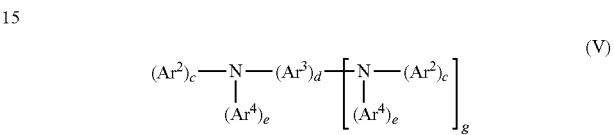

wherein $Ar^2$, $Ar^3$ and $Ar^4$ in each occurrence are independently selected from substituted or unsubstituted aryl or heteroaryl or a group of formula (IIa) wherein n2=0; g is 0, 1 or 2, preferably 0 or 1; and c, d and e are each independently 1, 2 or 3, wherein at least one of $Ar^2$, $Ar^3$ and $Ar^4$ is substituted with at least one group of formula (I), (IIa) or (IIb) and/or at least one of $Ar^2$ and $Ar^4$ is a group of formula (IIa) wherein n2=0.

Any two aromatic or heteroaromatic groups selected from $Ar^2$, $Ar^3$, $Ar^5$, and, if present, $Ar^4$ directly bound to the same N atom may be linked by a direct bond or a divalent linking atom or group. Preferred divalent linking atoms and groups include O, S; substituted N; and substituted C.

Preferably, each of $Ar^2$, $Ar^3$ and $Ar^4$ is independently an aryl group that, in addition to groups of formula (I), (IIa) and/or (IIb), may be unsubstituted or substituted with one or more substituents, optionally one or more $C_{1-20}$ alkyl or $C_{1-20}$ alkoxy groups.

Preferably, $Ar^2$ and $Ar^4$ are each independently phenyl or a group of formula (IIa) wherein n2=0.

In the case where g=1, $Ar^3$ is preferably $C_{6-20}$ aryl, more preferably phenyl or a polycyclic aromatic group, for example naphthalene, perylene, anthracene or fluorene. If $Ar^3$ is a polycyclic aromatic group then d is preferably 1.

Exemplary non-polymeric first and second compounds include the compounds illustrated below wherein $R^3$ in each occurrence is a substituent, optionally $C_{1-20}$ alkyl, and q is 0, 1, 2, 3 or 4.

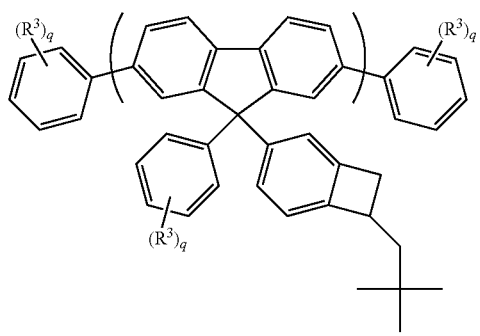

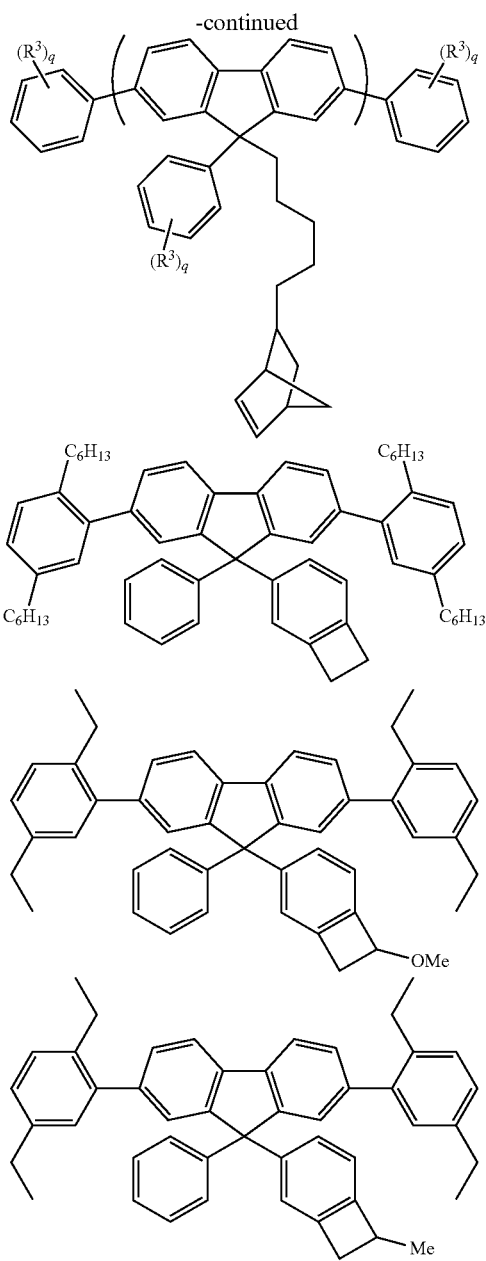

Repeat Units

Polymers comprising repeat units RU1 and/or RU2 are preferably copolymers comprising RU1 and/or RU2 and one or more co-repeat units. Co-repeat units preferably do not comprise crosslinkable groups.

Preferably, RU1 and RU2 comprise at least one aromatic or heteroaromatic group, more preferably at least one aromatic group. Preferably, polymers comprising repeat units RU1 and/or RU2 are conjugated polymers.

Optionally, RU1 and RU2 are selected from hole-transporting repeat units, electron-transporting repeat units and light-emitting repeat units.

RU1 and RU2 may be selected according to the function of the layer that they are to be present in or may be used in combination with co-repeat units providing the required functionality. For example, a hole-transporting polymer for use in a hole-transporting layer may contain a hole-transporting repeat unit RU1 or RU2 or may contain a hole-transporting co-repeat unit.

Exemplary repeat units of conjugated polymers are arylene repeat units, arylenevinylene repeat units and arylamine repeat units, each of which may be a co-repeat unit or a repeat unit of formula (IIIc), (IIId), (IVc) or (IVd) wherein RU1 or RU2 is arylene, arylenevinylene or arylamine.

One preferred class of arylene repeat units is phenylene repeat units, such as phenylene repeat units of formula (VI):

(VI)

wherein w in each occurrence is independently 0, 1, 2, 3 or 4, optionally 1 or 2; n is 1, 2 or 3; and $R^7$ independently in each occurrence is a substituent.

Where present, each $R^7$ may independently be selected from the group consisting of:

alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F;

aryl and heteroaryl groups that may be unsubstituted or substituted with one or more substituents, preferably phenyl substituted with one or more $C_{1-20}$ alkyl groups;

a linear or branched chain of aryl or heteroaryl groups, each of which groups may independently be substituted, for example a group of formula —$(Ar^7)_r$ wherein each $Ar^7$ is independently an aryl or heteroaryl group and r is at least 2, preferably a branched or linear chain of phenyl groups each of which may be unsubstituted or substituted with one or more $C_{1-20}$ alkyl groups; and a group of formula (I), (IIa) or (IIb).

In the case where $R^7$ comprises an aryl or heteroaryl group, or a linear or branched chain of aryl or heteroaryl groups, the or each aryl or heteroaryl group may be substituted with one or more substituents $R^8$ selected from the group consisting of:

alkyl, for example $C_{1-20}$ alkyl, wherein one or more non-adjacent C atoms may be replaced with O, S, substituted N, C=O and —COO— and one or more H atoms of the alkyl group may be replaced with F;

$NR^9_2$, $OR^9$, $SR^9$, $SiR^9_3$ and fluorine, nitro and cyano;

wherein each $R^9$ is independently selected from the group consisting of alkyl, preferably $C_{1-20}$ alkyl; and aryl or heteroaryl, preferably phenyl, optionally substituted with one or more $C_{1-20}$ alkyl groups.

Substituted N, where present, may be —$NR^6$— wherein $R^6$ is a substituent and is optionally a $C_{1-40}$ hydrocarbyl group, optionally a $C_{1-20}$ alkyl group.

Preferably, each $R^7$, where present, is independently selected from a group of formula (I), (IIa) or (IIb), and $C_{1-40}$ hydrocarbyl. Preferred $C_{1-40}$ hydrocarbyl groups are $C_{1-20}$ alkyl; unsubstituted phenyl; phenyl substituted with one or more $C_{1-20}$ alkyl groups; and a linear or branched chain of phenyl groups, wherein each phenyl may be unsubstituted or substituted with one or more substituents.

If n is 1 then exemplary repeat units of formula (VI) include the following:

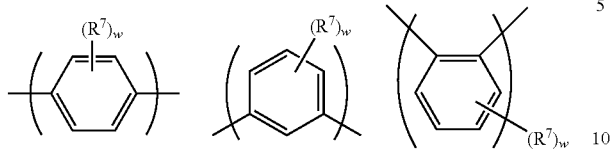

A particularly preferred repeat unit of formula (VI) has formula (VIa):

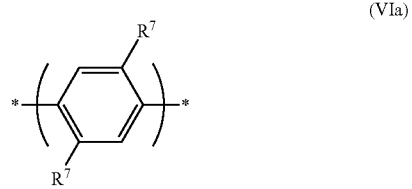

Substituents $R^7$ of formula (VIa) are adjacent to linking positions of the repeat unit, which may cause steric hindrance between the repeat unit of formula (VIa) and adjacent repeat units, resulting in the repeat unit of formula (VIa) twisting out of plane relative to one or both adjacent repeat units.

Exemplary repeat units where n is 2 or 3 include the following:

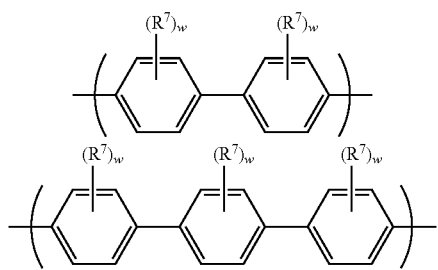

A preferred repeat unit has formula (VIb):

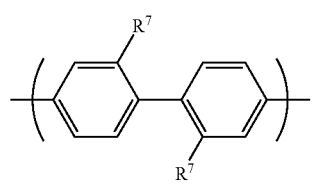

The two $R^7$ groups of formula (VIb) may cause steric hindrance between the phenyl rings they are bound to, resulting in twisting of the two phenyl rings relative to one another.

A further class of arylene repeat units is optionally substituted fluorene repeat units, such as repeat units of formula (VII):

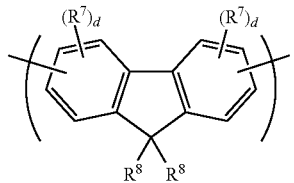

wherein $R^8$ in each occurrence is the same or different and is a substituent wherein the two groups $R^8$ may be linked to form a ring; $R^7$ is a substituent as described above; and d is 0, 1, 2 or 3.

Each $R^8$ may independently be selected from the group consisting of:

alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F;

aryl and heteroaryl groups that may be unsubstituted or substituted with one or more substituents, preferably phenyl substituted with one or more $C_{1-20}$ alkyl groups;

a linear or branched chain of aryl or heteroaryl groups, each of which groups may independently be substituted, for example a group of formula —$(Ar^7)_r$ wherein each $Ar^7$ is independently an aryl or heteroaryl group and r is at least 2, optionally 2 or 3, preferably a branched or linear chain of phenyl groups each of which may be unsubstituted or substituted with one or more $C_{1-20}$ alkyl groups; and a group of formula (I), (IIa) or (IIb).

Preferably, each $R^8$ is independently a group of formula (I), (IIa) or (IIb) or a $C_{1-40}$ hydrocarbyl group. Preferred $C_{1-40}$ hydrocarbyl groups are $C_{1-20}$ alkyl; unsubstituted phenyl; phenyl substituted with one or more $C_{1-20}$ alkyl groups; and a linear or branched chain of phenyl groups, wherein each phenyl may be unsubstituted or substituted with one or more substituents.

Substituted N, where present, may be —$NR^6$— wherein $R^6$ is as described above.

The aromatic carbon atoms of the fluorene repeat unit may be unsubstituted, or may be substituted with one or more substituents $R^7$ as described with reference to Formula (VI).

Exemplary substituents $R^7$ are alkyl, for example $C_{1-20}$ alkyl, wherein one or more non-adjacent C atoms may be replaced with O, S, C=O and —COO—, optionally substituted aryl, optionally substituted heteroaryl, alkoxy, alkylthio, fluorine, cyano and arylalkyl. Particularly preferred substituents include $C_{1-20}$ alkyl and substituted or unsubstituted aryl, for example phenyl. Optional substituents for the aryl include one or more $C_{1-20}$ alkyl groups.

The extent of conjugation of repeat units of formula (VII) to aryl or heteroaryl groups of adjacent repeat units in the polymer backbone may be controlled by (a) linking the repeat unit through the 3- and/or 6-positions to limit the extent of conjugation across the repeat unit, and/or (b) substituting the repeat unit with one or more substituents $R^7$ in or more positions adjacent to the linking positions in order to create a twist with the adjacent repeat unit or units, for example a 2,7-linked fluorene carrying a $C_{1-20}$ alkyl substituent in one or both of the 3- and 6-positions.

The repeat unit of formula (VII) may be a 2,7-linked repeat unit of formula (VIIa):

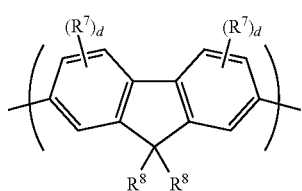

(VIIa)

A relatively high degree of conjugation across the repeat unit of formula (VIIa) may be provided in the case where each d=0, or where any substituent $R^7$ is not present at a position adjacent to the linking 2- or 7-positions of formula (VIIa).

A relatively low degree of conjugation across the repeat unit of formula (VIIa) may be provided in the case where at least one d is at least 1, and where at least one substituent $R^7$ is present at a position adjacent to the linking 2- or 7-positions of formula (VIIa). Optionally, each d is 1 and the 3- and/or 6-position of the repeat unit of formula (VIIa) is substituted with a substituent $R^7$ to provide a relatively low degree of conjugation across the repeat unit.

The repeat unit of formula (VII) may be a 3,6-linked repeat unit of formula (VIIb)

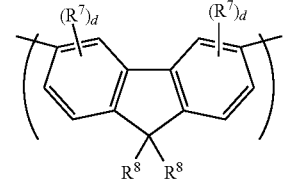

(VIIb)

The extent of conjugation across a repeat unit of formula (VIIb) may be relatively low as compared to a corresponding repeat unit of formula (VIIa).

Another exemplary arylene repeat unit has formula (VIII):

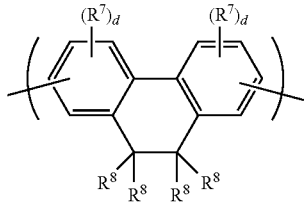

(VIII)

wherein $R^7$, $R^8$ and d are as described with reference to formulae (VI) and (VII) above. Any of the $R^7$ groups may be linked to any other of the $R^7$ groups to form a ring. The ring so formed may be unsubstituted or may be substituted with one or more substituents, optionally one or more $C_{1-20}$ alkyl groups.

Repeat units of formula (VIII) may have formula (VIIIa) or (VIIIb):

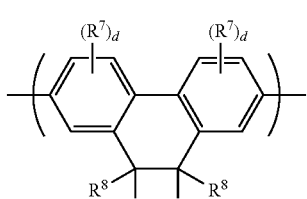

(VIIIa)

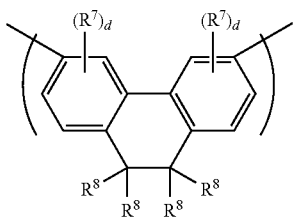

(VIIIb)

The one or more co-repeat units may include a conjugation-breaking repeat unit, which is a repeat unit that does not provide any conjugation path between repeat units adjacent to the conjugation-breaking repeat unit.

Exemplary conjugation-breaking co-repeat units include co-repeat units of formula (IX):

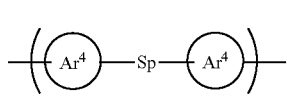

(IX)

wherein:
$Ar^4$ in each occurrence independently represents an aryl or heteroaryl group that may be unsubstituted or substituted with one or more substituents; and
Sp represents a spacer group comprising at least one carbon or silicon atom.

Preferably, the spacer group Sp includes at least one $sp^3$-hybridised carbon atom separating the $Ar^4$ groups.

Preferably $Ar^4$ is an aryl group and the $Ar^4$ groups may be the same or different. More preferably each $Ar^4$ is phenyl.

Each $Ar^4$ may independently be unsubstituted or may be substituted with 1, 2, 3 or 4 substituents. The one or more substituents may be selected from:
  $C_{1-20}$ alkyl wherein one or more non-adjacent C atoms of the alkyl group may be replaced by O, S or COO, C=O, $NR^6$ or $SiR^6_2$, and one or more H atoms of the $C_{1-20}$ alkyl group may be replaced by F wherein $R^6$ is a substituent and is optionally in each occurrence a $C_{1-40}$ hydrocarbyl group, optionally a $C_{1-20}$ alkyl group; and
  aryl or heteroaryl, optionally phenyl, that may be unsubstituted or substituted with one or more $C_{1-20}$ alkyl groups.

Preferred substituents of $Ar^4$ are $C_{1-20}$ alkyl groups, which may be the same or different in each occurrence.

Exemplary groups Sp include a $C_{1-20}$ alkyl chain wherein one or more non-adjacent C atoms of the chain may be replaced with O, S, —$NR^6$—, —$SiR^6_2$—, —C(=O)— or —COO— and wherein $R^6$ in each occurrence is a substituent and is optionally in each occurrence a $C_{1-40}$ hydrocarbyl group, optionally a $C_{1-20}$ alkyl group. Preferably, Sp contains at least one sp3-hybridised carbon atom spacing the two groups $Ar^4$ apart.

A polymer comprising a repeat unit RU1 and/or RU2 may comprise arylamine repeat units of formula (X), either as a co-repeat unit or a repeat unit of formula (IIIc), (IIId), (IVc) or (IVd):

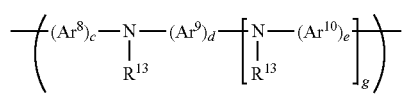
(X)

wherein $Ar^8$, $Ar^9$ and $Ar^{10}$ in each occurrence are independently selected from substituted or unsubstituted aryl or heteroaryl, g is 0, 1 or 2, preferably 0 or 1, $R^{13}$ independently in each occurrence is H or a substituent, preferably a substituent, and c, d and e are each independently 1, 2 or 3.

Repeat units of formula (X) may provide the polymer with hole-transporting properties for use in a hole-transporting layer or light-emitting layer, and/or light-emitting properties for use in a light-emitting layer $R^{13}$, which may be the same or different in each occurrence when g is 1 or 2, is preferably selected from the group consisting of alkyl, for example $C_{1-20}$ alkyl, $Ar^{11}$, a branched or linear chain of $Ar^{11}$ groups, or a group of formula (I), (IIa) or (IIb), wherein $Ar^{11}$ in each occurrence is independently optionally substituted aryl or heteroaryl.

Any two aromatic or heteroaromatic groups selected from $Ar^8$, $Ar^9$, and, if present, $Ar^{10}$ and $Ar^{11}$ directly bound to the same N atom may be linked by a direct bond or a divalent linking atom or group to another of $Ar^8$, $Ar^9$, $Ar^{10}$ and $Ar^{11}$. Preferred divalent linking atoms and groups include O, S; substituted N; and substituted C.

$Ar^8$ and $Ar^{10}$ are preferably $C_{6-20}$ aryl, more preferably phenyl, that may be unsubstituted or substituted with one or more substituents.

In the case where g=0, $Ar^9$ is preferably $C_{6-20}$ aryl, more preferably phenyl, that may be unsubstituted or substituted with one or more substituents.

In the case where g=1, $Ar^9$ is preferably $C_{6-20}$ aryl, more preferably phenyl or a polycyclic aromatic group, for example naphthalene, perylene, anthracene or fluorene, that may be unsubstituted or substituted with one or more substituents.

$R^{13}$ is preferably $Ar^{11}$ or a branched or linear chain of $Ar^{11}$ groups. $Ar^{11}$ in each occurrence is preferably phenyl that may be unsubstituted or substituted with one or more substituents.

Exemplary groups $R^{13}$ include the following, each of which may be unsubstituted or substituted with one or more substituents, and wherein * represents a point of attachment to N:

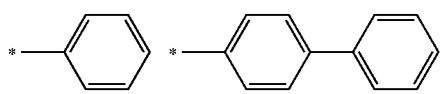

-continued

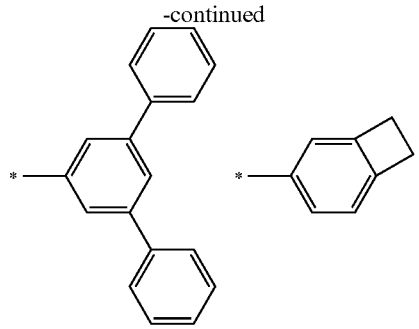

c, d and e are preferably each 1.

$Ar^8$, $Ar^9$, and, if present, $Ar^{10}$ and $Ar^{11}$ are each independently unsubstituted or substituted with one or more, optionally 1, 2, 3 or 4, substituents. Exemplary substituents may be selected from:
  substituted or unsubstituted alkyl, optionally $C_{1-20}$ alkyl, wherein one or more non-adjacent C atoms may be replaced with optionally substituted aryl or heteroaryl (preferably phenyl), O, S, C=O or —COO— and one or more H atoms may be replaced with F; and
  a group of formula (I), (IIa) or (IIb).

Preferred substituents of $Ar^8$, $Ar^9$, and, if present, $Ar^{10}$ and $Ar^{11}$ are $C_{1-40}$ hydrocarbyl, preferably $C_{1-20}$ alkyl or a group of formula (I), (IIa) or (IIb).

Preferred repeat units of formula (IX) include unsubstituted or substituted units of formulae 1-3:

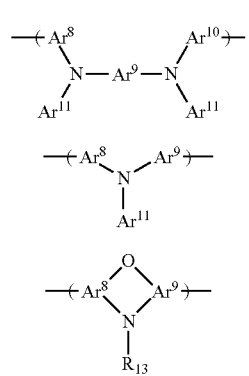

Preferably, $Ar^8$, $Ar^{10}$ and $Ar^{11}$ of repeat units of formula 1 are phenyl and $Ar^9$ is phenyl or a polycyclic aromatic group.

Preferably, $Ar^8$, $Ar^9$ and $Ar^{11}$ of repeat units of formulae 2 and 3 are phenyl.

Preferably, $Ar^8$ and $Ar^9$ of repeat units of formula 3 are phenyl and $R^{13}$ is phenyl or a branched or linear chain of phenyl groups.

A hole-transporting polymer comprising repeat units of formula (X) may be a homopolymer or a copolymer containing repeat units of formula (X) and one or more co-repeat units.

Repeat units of formula (X) may be provided in a molar amount in the range of about 10 mol % up to about 95 mol %, optionally about 10-75 mol % or about 10-50 mol %.

The polymer may contain one or two or more different repeat units of formula (X).

Exemplary polymeric repeat units of formulae (IIIc), (IIId), (IVc) and (IVd) are illustrated below.

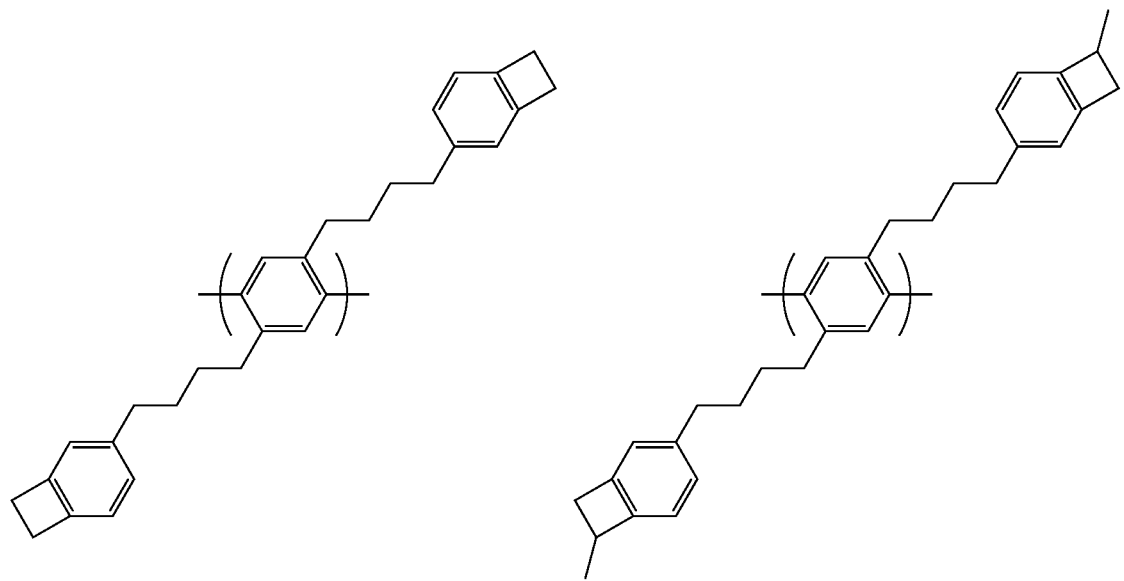
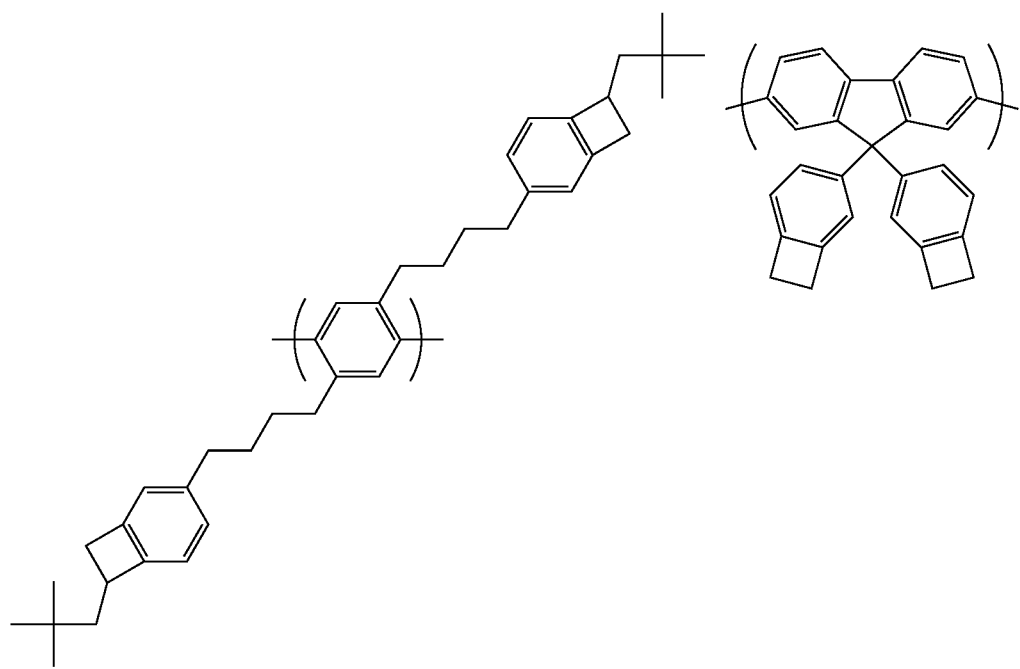

25
-continued
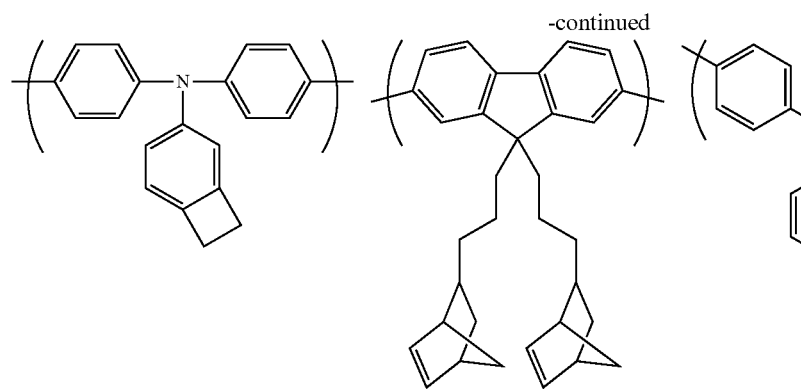
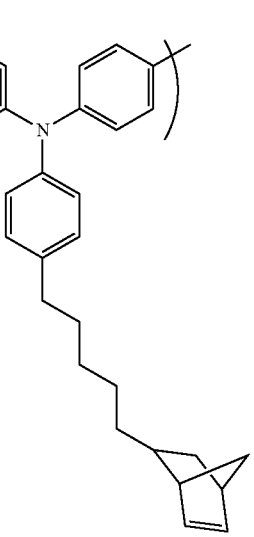
26
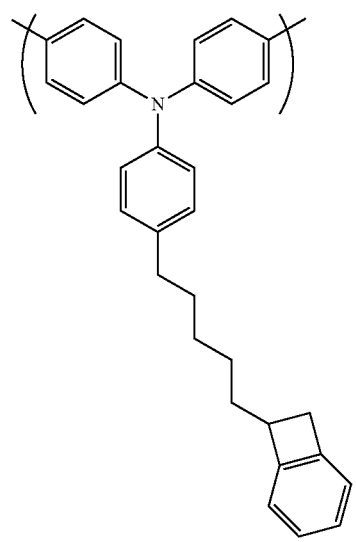
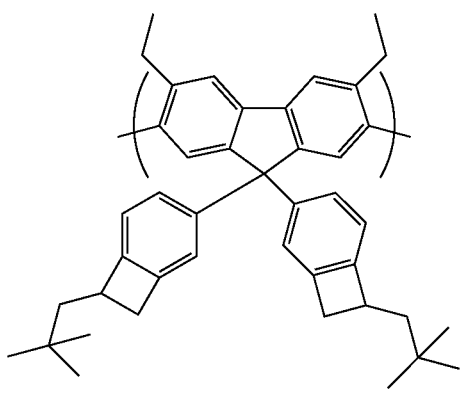
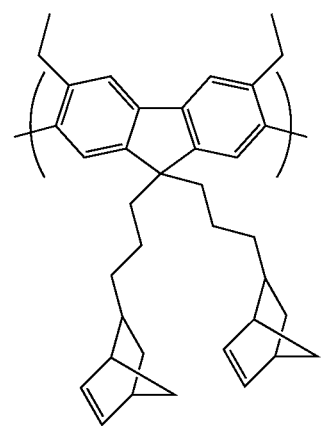
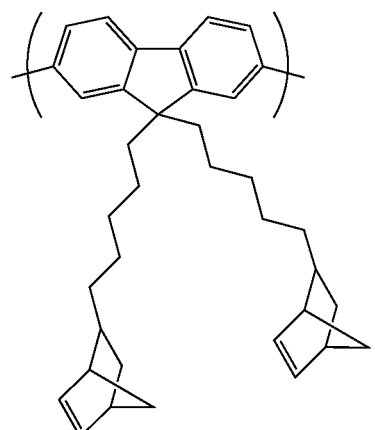
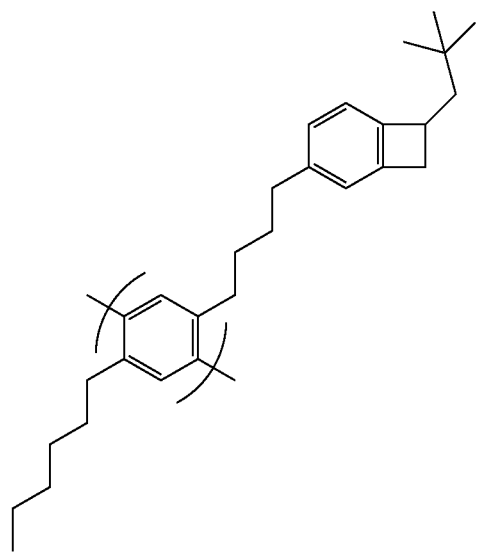

-continued
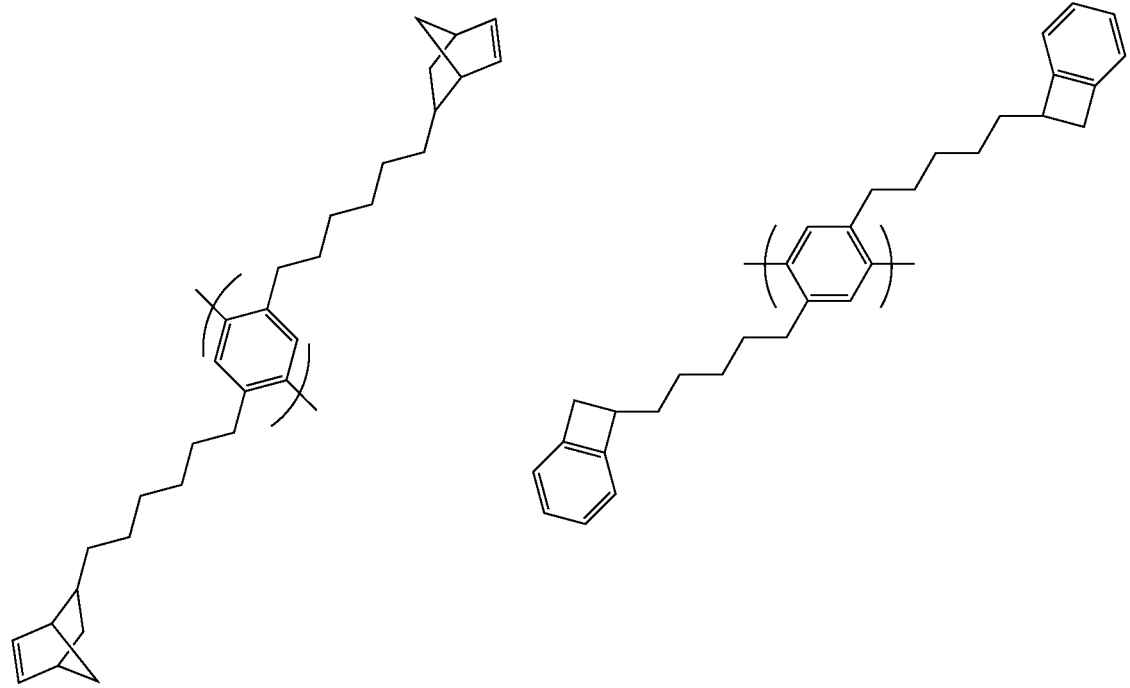
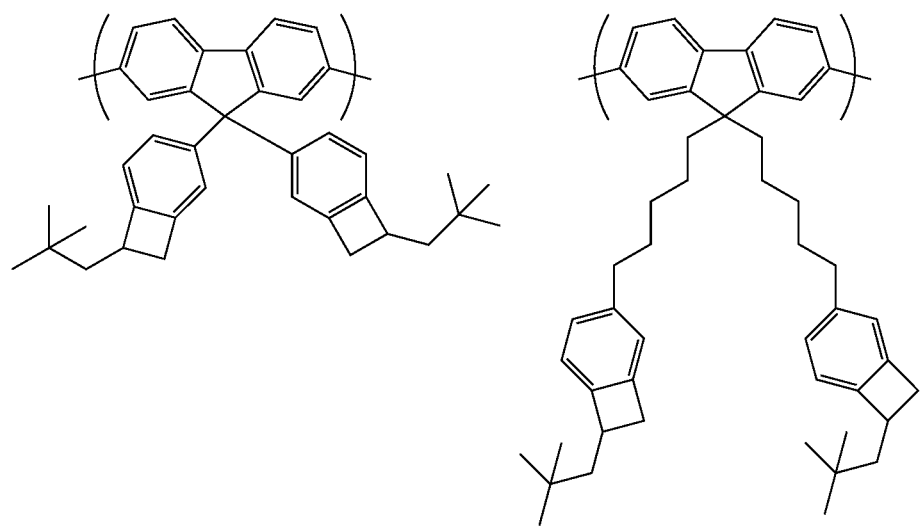

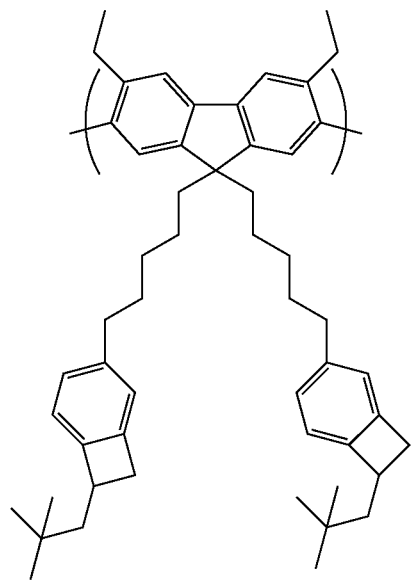
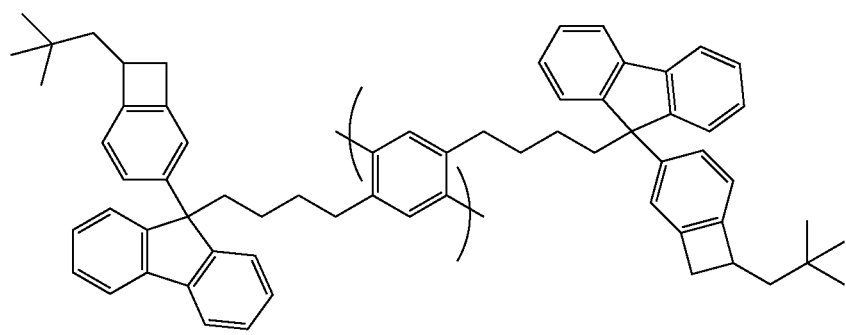
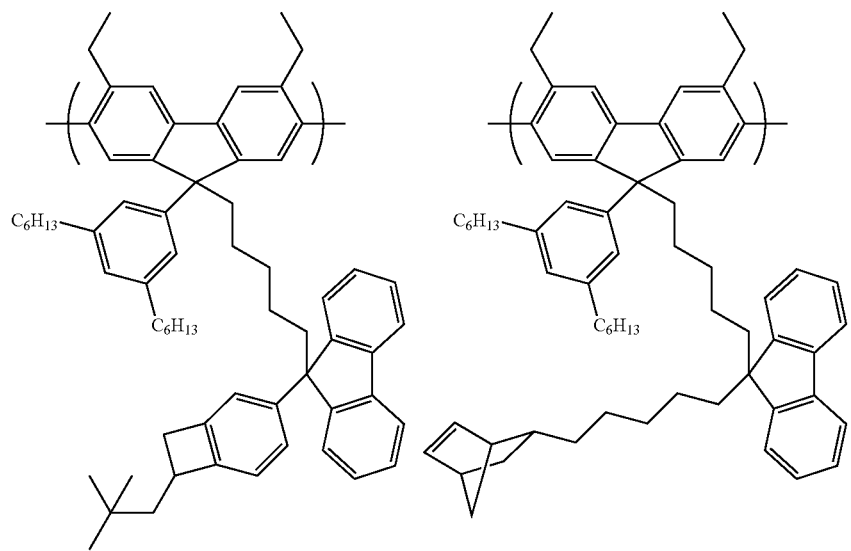

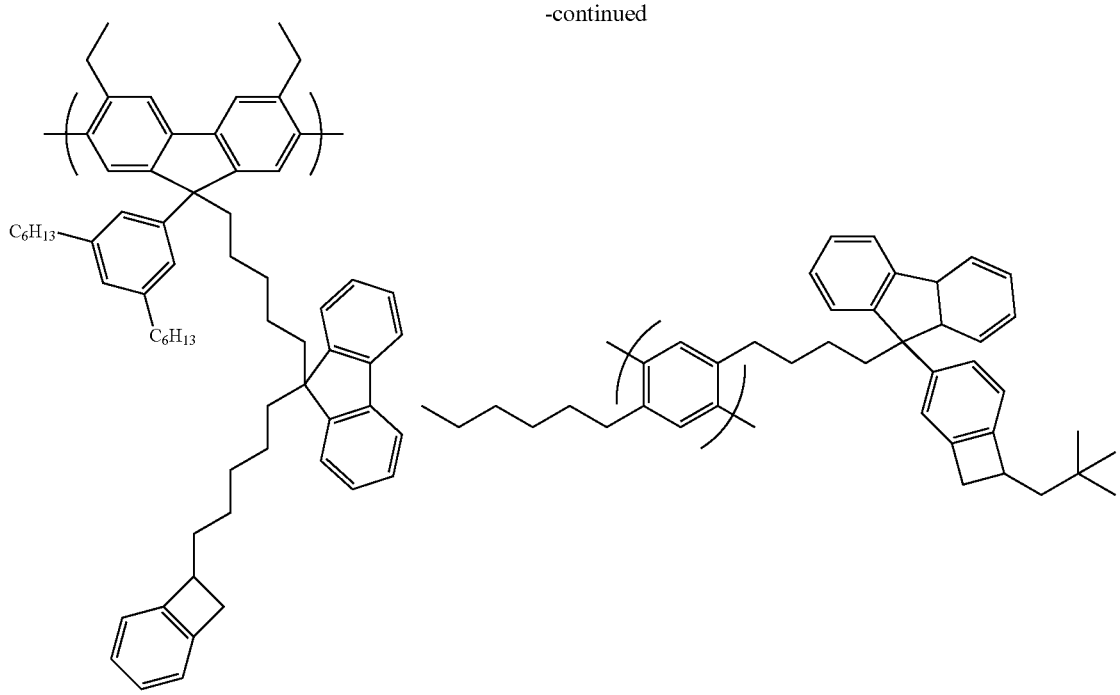

If repeat units of formula (IIIc) and repeat units of formula (IVc) or (IVd) are repeat units of the same polymer then a co-repeat unit that does not comprise a crosslinkable group may be provided between units of formula (IIIc) and the units of formula (IVc) or (IVd) to prevent crosslinkable substituents of the same polymer chain reacting with each other. Repeat units of formula (IIIc) and repeat units of formula (IVc) or (IVd) may be kept apart using polymerisation methods known to the skilled person. In the case where the polymer is formed by Suzuki polymerisation, repeat units of formula (IIIc) and repeat units of formula (IVc) or (IVd) may be separated by a non-crosslinking co-repeat unit if the monomers for forming repeat units of formula (IIIc) and repeat units of formula (IVc) or (IVd) comprise reactive leaving groups selected from one of halogen and boronic acid or ester, and the co-repeat unit or units comprise leaving groups selected from the other of halogen and boronic acid or ester.

Polymers as described herein suitably have a polystyrene-equivalent number-average molecular weight (Mn) measured by gel permeation chromatography in the range of about $1 \times 10^3$ to $1 \times 10^8$, and preferably $1 \times 10^3$ to $5 \times 10^6$. The polystyrene-equivalent weight-average molecular weight (Mw) of the polymers described herein may be $1 \times 10^3$ to $1 \times 10^8$, and preferably $1 \times 10^4$ to $1 \times 10^7$.

The polymers as described anywhere herein are suitably amorphous polymers.

Polymer Synthesis

Preferred methods for preparation of conjugated polymers comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable π-Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end group or side group may be bound to the polymer by reaction of a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halogen, other leaving groups capable of participating in metal insertion include groups include tosylate, mesylate and triflate.

Hole Injection Layers

A conductive hole injection layer, which may be formed from a conductive organic or inorganic material, may be provided between the anode 103 and the hole-transporting layer 105 of an OLED as illustrated in FIG. 1 to assist hole injection from the anode into the layer or layers of semiconducting polymer. Examples of doped organic hole injection materials include optionally substituted, doped poly (ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and U.S. Pat. No. 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Cathode

The cathode 109 is selected from materials that have a workfunction allowing injection of electrons into the light-emitting layer of the OLED. Other factors influence the selection of the cathode such as the possibility of adverse interactions between the cathode and the light-emitting material. The cathode may consist of a single material such as a layer of aluminium. Alternatively, it may comprise a plurality of conductive materials such as metals, for example a bilayer of a low work function material and a high work function material such as calcium and aluminium, for example as disclosed in WO 98/10621. The cathode may comprise elemental barium, for example as disclosed in WO 98/57381, Appl. Phys. Lett. 2002, 81(4), 634 and WO 02/84759. The cathode may comprise a thin (e.g. 1-5 nm) layer of metal compound, in particular an oxide or fluoride of an alkali or alkali earth metal, between the organic layers of the device and one or more conductive cathode layers to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a work function of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Formulation Processing

A formulation suitable for forming a layer of an organic electronic device, preferably a layer of an OLED, more preferably a hole-transporting layer of an OLED, may be formed from the composition of the invention and one or more suitable solvents. In the case of an OLED hole-transporting layer, a light-emitting layer may be formed on the hole-transporting layer by a solution deposition technique as described herein.

The formulation may be a solution of the composition in the one or more solvents, or may be a dispersion in the one or more solvents in which one or more components are not dissolved. Preferably, the formulation is a solution.

Solvents suitable for dissolving compositions of the invention, particularly compositions containing polymers comprising alkyl substituents, include benzenes substituted with one or more $C_{1-10}$ alkyl or $C_{1-10}$ alkoxy groups, for example toluene, xylenes and methylanisoles.

Particularly preferred solution deposition techniques include printing and coating techniques such as spin-coating and inkjet printing.

Spin-coating is particularly suitable for devices wherein patterning of the light-emitting layer is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is preferably a layer of photoresist that is patterned to define wells as described in, for example, EP 0880303. A hole-transporting layer may be formed by inkjet printing a material or composition as described herein into the wells of the patterned layer and reacting, preferably crosslinking, the material. The light-emitting material or materials may then be inkjet printed into the wells on the hole-transporting layer.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, flexographic printing and screen printing.

Applications

Compositions as described herein may be used to form one or more layers of organic electronic devices. Preferably, a composition as described herein is used to form a cross-linked layer onto which a further layer is formed by a solution deposition method.

Compositions and layer formation methods as described herein may be used to form a charge-transporting layer or light-emitting layer of an OLED; a semiconducting layer of an organic photoresponsive device, for example a photosensor or a photoresponsive device; and a semiconducting layer or dielectric layer of an organic thin film transistor.

An organic photoresponsive device may comprise an anode, a cathode and a semiconducting layer formed from a composition as described herein between the anode and the cathode. The organic semiconducting layer may be an electron accepting layer, an electron-donating layer, or a further layer between the anode and the cathode. A single layer containing a blend of an electron-accepting material and an electron-donating material may be provided in place of separate accepting and donating layers, and this layer may be crosslinked by substituting one or more components of this layer with at least one substituent of formula (I) and optionally at least one substituent of formula (IIa) or (IIb).

An organic thin film transistor may comprise source and drain electrodes; an organic semiconductor layer extending between and in electrical contact with the source and drain electrodes; a gate electrode; and a dielectric layer between the organic semiconducting layer and the gate electrode.

EXAMPLES

Compound Example 1

Non-polymeric Compound Example 1 was prepared according to the following reaction scheme:

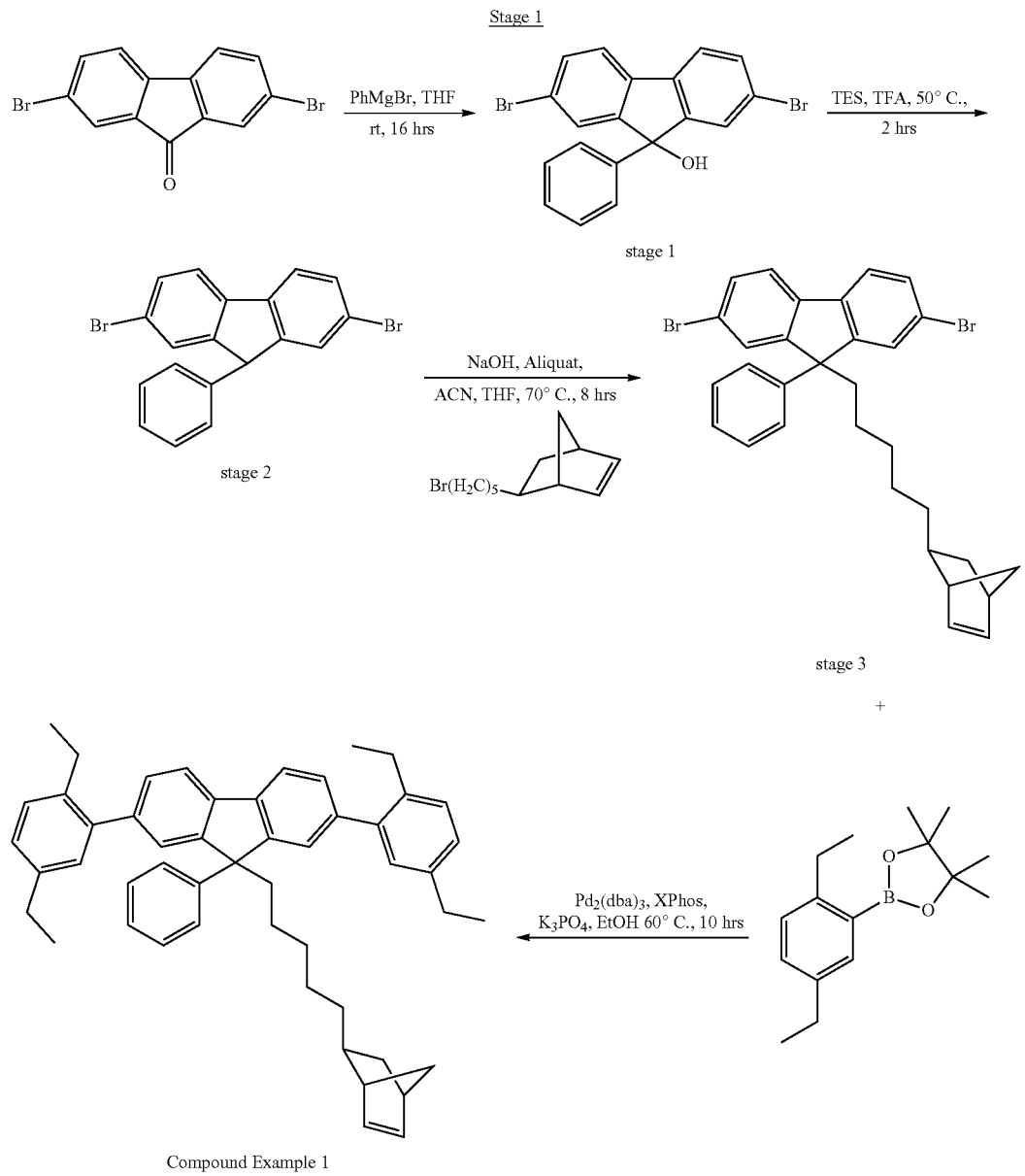

Compound Example 1

To a solution of magnesium turnings (10.77 g, 0.45 mol) and 1,2-dibromoethane (0.5 ml) in diethyl ether (125 mL) was added bromobenzene (46.44 g, 0.295 mol) drop wise slowly at room temperature and the mixture was stirred at this temperature for a further 2 hrs. The resulting Grignard reagent was added drop wise to a solution of 2,7-dibromo-flurenone (25 g, 0.074 mol) in anhydrous THF (500 ml) at 0° C. and the reaction was stirred for a further 5 hrs at this temperature. The mixture was quenched with ice-cold water (100 ml), extracted with EtOAc (2×300 ml) and the combined organic extracts were washed with brine (500 ml), dried ($Na_2SO_4$) and concentrated under vacuum. Purification by silica gel column chromatography (2% EtOAc/hexane) gave stage 1 product (23 g, 75% yield, 97.8% HPLC purity).

MS (EI, m/z): 416 ($M^+$), 399, 337, 258, 239, 226, 167, 151

$^1$H-NMR (300 MHz, DMSO-$d_6$): $\delta_H$ [ppm] 6.64 (s, 1H), 7.21-7.29 (m, 5H), 7.33 (d, J =1.32 Hz, 2H), 7.58 (dd, J=1.32, 8.08 Hz, 2H), 7.83 (d, J=8.10 Hz, 2H).

Stage 2

To a solution of XL15 stage 1 (23 g, 0.055 mol) in trifluoroacetic acid (230 ml) was added triethyl silane (32.13 g, 0.276 mol) drop wise and the reaction mixture stirred at 50° C. for 2 hrs. The mixture was allowed to cool to room temperature, the trifluoroacetic acid was removed under vacuum and the resulting solid treated with an aqueous solution of $NaHCO_3$ (300 ml), extracted with EtOAc (2×300 ml), washed with brine (300 ml), dried ($Na_2SO_4$) and concentrated under vacuum. The solid was stirred over methanol (100 ml) and subsequent filtration gave the desired product stage 2 product (19 g, 86% yield, 96.9% HPLC purity).

MS (EI, m/z): 400 ($M^+$), 319, 239, 163, 120

$^1$H-NMR (400 MHz, $CDCl_3$): $\delta_H$ [ppm] 5.02 (s, 1H), 7.05-7.07 (m, 2H), 7.28-7.34 (m, 3H), 7.43 (s, 2H), 7.51-7.54 (m, 2H), 7.64 (d, J=8.12 Hz, 2H).

Stage 3

To a solution of XL15 stage 2 (14 g, 0.035 mol), and 5-(5-bromopenyt-1-yl) bicyclo[2.2.1] hept-2-ene (19.57 g, 0.080 mol) in THF:ACN (175 ml, 4:1), was added Aliquat-336 (0.707 g, 0.002 mol) followed by an aqueous solution of NaOH (56 ml, 10% wt/vol) and the mixture heated at 70° C. for 5 hrs. After cooling to room temperature, water (150 ml) was added and the mixture extracted with EtOAc (2×250 ml), the combined organic extracts were dried ($Na_2SO_4$) and concentrated in vacuum. Purification by silica gel column chromatography (1% EtOAc/hexane) gave stage 3 product (10 g, 51% yield, 97.9% HPLC purity).

MS (EI, m/z): 562 ($M^+$), 496, 399, 239

$^1$H-NMR (300 MHz, $CDCl_3$): $\delta_H$ [ppm] 0.42-0.46 (m, 1H), 0.80-0.98 (m, 4H), 1.22-1.43 (m, 5H), 1.74-1.93 (m, 3H), 2.37-2.43 (m, 2H), 2.69-2.75 (m, 2H), 5.84-5.87 (m, 1H), 6.05-6.09 (m, 1H), 7.11-7.27 (m, 7H), 7.26-7.27 (m, 2H), 7.31-7.38 (m, 2H).

Compound Example 1

A mixture of XL15 stage 3 (8 g, 0.014 mol), 2-(2,5-diethylphenyl)-4,4,5,5-tetramethyl-1,3,2-dioxaborolane (9.2 g, 0.035 mol), $K_3PO_4.H_2O$ (9.8 g, 0.043 mol), $Pd_2(dba)_3$ (0.389 g, 0.0004 mol), and XPhos (0.406 g, 0.0008 mol) in ethanol (160 ml) in a sealed tube was purged with $N_2$ for 5 mins and heated at 60° C. for 12 hrs. The reaction mixture was cooled to room temperature, passed through a Celite plug; the filtrate was concentrated under vacuum to give a brown solid. Purification by silica gel column chromatography (hexane), followed by reverse phase column chromatography (6% THF:acetonitrile) gave Compound Example 1 as a clear viscous oil (4.78 g, 51% yield, 99.4% HPLC purity).

LCMS (APPI, m/z): 669 ($M^+$)

$^1$H-NMR (400 MHz, $CDCl_3$): $\delta_H$ [ppm] 0.41-0.44 (m, 1H), 0.87-0.96 (m, 4H), 1.06 (t, J=7.20 Hz, 3H), 1.17-1.21 (m, 4H), 1.28 (t, J=7.60 Hz, 3H), 1.31-1.34 (m, 2H), 1.79-1.92 (m, 2H), 2.48-2.53 (m, 4H), 2.65-2.69 (m, 4H), 5.83-5.85 (m, 1H), 6.05-6.07 (m, 1H), 7.12-7.29 (m, 13H), 7.35 (d, J=8.00 Hz, 2H), 7.83 (d, J=7.60 Hz, 2H).

The other non-polymeric compounds disclosed herein can be prepared as described above using side chains selected from 5-bromopentene, 3-bromo bicyclo[4.2.0]octa-1,3,5-triene, 3-bromo-7-methylbicyclo[4.2.0]octa-1,3,5-triene or 3-bromo-7 methoxybicyclo[4.2.0]octa-1,3,5-triene instead of 5-(5-bromopenyt-1-yl) bicyclo[2.2.1] hept-2-ene.

Monomer Example 1

Monomer Example 1 was prepared according to the following reaction scheme:

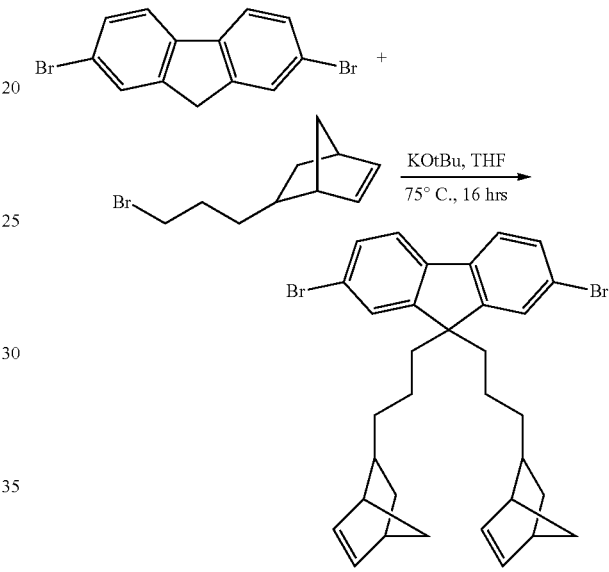

Monomer Example 1

To a solution of 2,7-dibromo-9H-fluorene (2 g, 6.17 mmol) in dry THF (20 ml) under nitrogen, was added potassium tert-butoxide (3.4 g, 30.86 mol) and the mixture stirred at 70° C. for 2 hrs. The reaction mixture was cooled to room temperature, 5-(3-bromoprop-1-yl)-bicyclo[2.2.1] hept-2-ene (3.9 g, 18.52 mol) in dry THF (5 ml) was added drop wise and then the mixture was stirred at 75° C. for 16 hrs. On cooling, water (50 ml) was added and the solution extracted with dichloromethane (2×50 ml). The combined organic extracts were washed with water (50 ml), brine (50 ml), dried ($Na_2SO_4$) and concentrated under reduced pressure to give an yellow solid. Purification by silica gel column chromatography (hexane) gave a solid which was triturated with a mixture of MeOH/EtOAc (5 ml:3 ml) at 50° C. for 30 mins. The solid was filtered and washed with methanol to give Monomer Example 1 as a white solid (1.16 g, 32% yield, 99.8% purity by HPLC).

$^1$H-NMR (400 MHz, $CDCl_3$): $\delta_H$ [ppm] 0.26-0.30 (m, 2H), 0.57-0.63 (m, 4H), 0.82-0.87 (m, 4H), 1.09-1.19 (m, 2H), 1.27-1.29 (m, 2H), 1.64-1.69 (m, 2H), 1.71-1.76 (m, 2H), 1.86-1.92 (m, 4H), 2.50 (m, 2H,), 2.66 (m, 2H), 5.72 (dd, J=2.8 Hz, 5.6 Hz, 2H), 6.03 (dd, J=2.9 Hz, 5.6 Hz, 2H), 7.45-7.49 (m, 4H), 7.54-7.56 (m, 2H).

Monomer B

Monomer B was prepared according to the following reaction scheme:

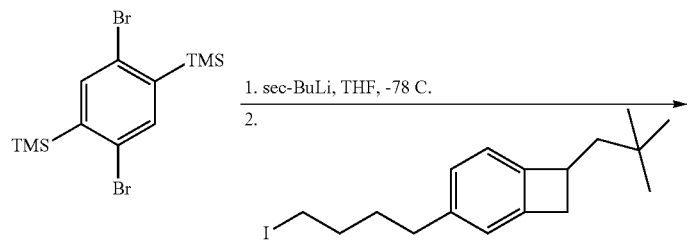
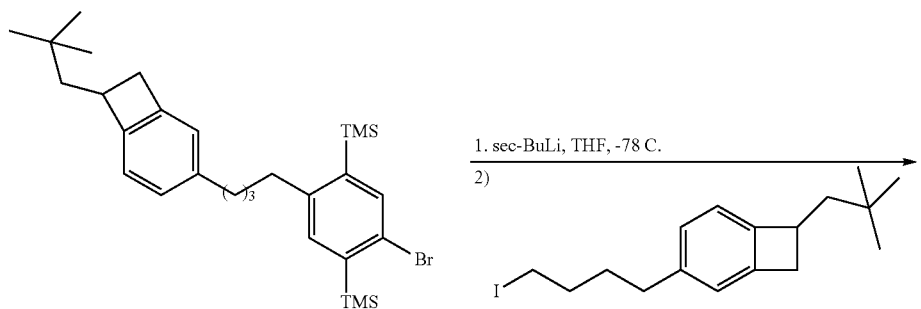
Monomer B Stage 1
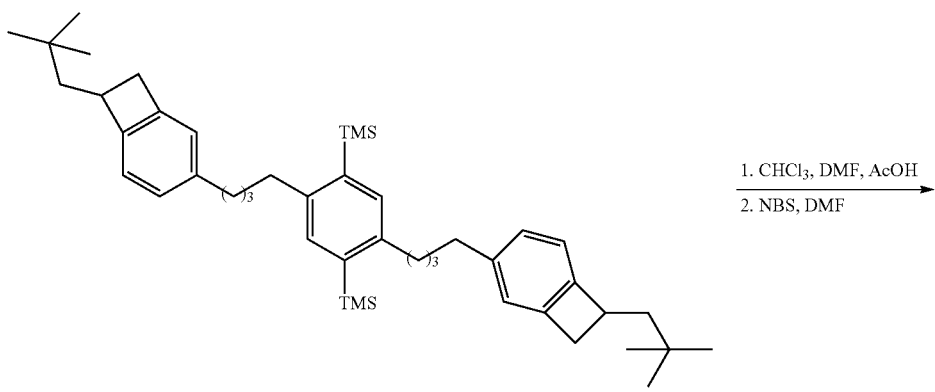
Monomer B Stage 2
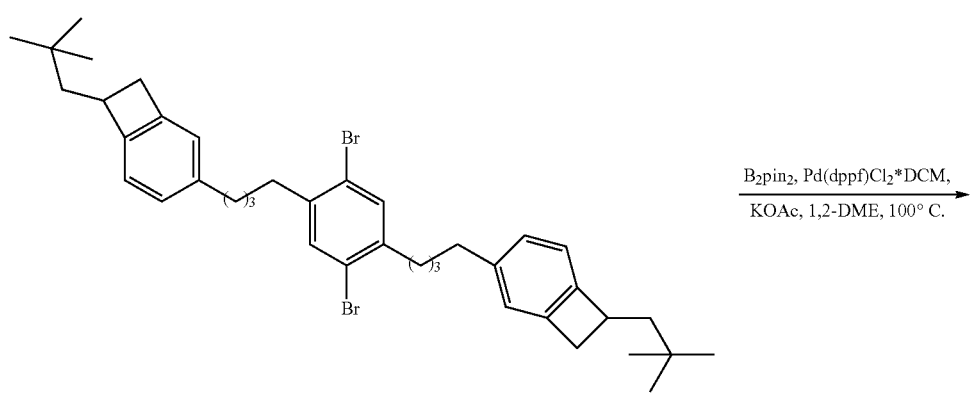
Monomer B Stage 3

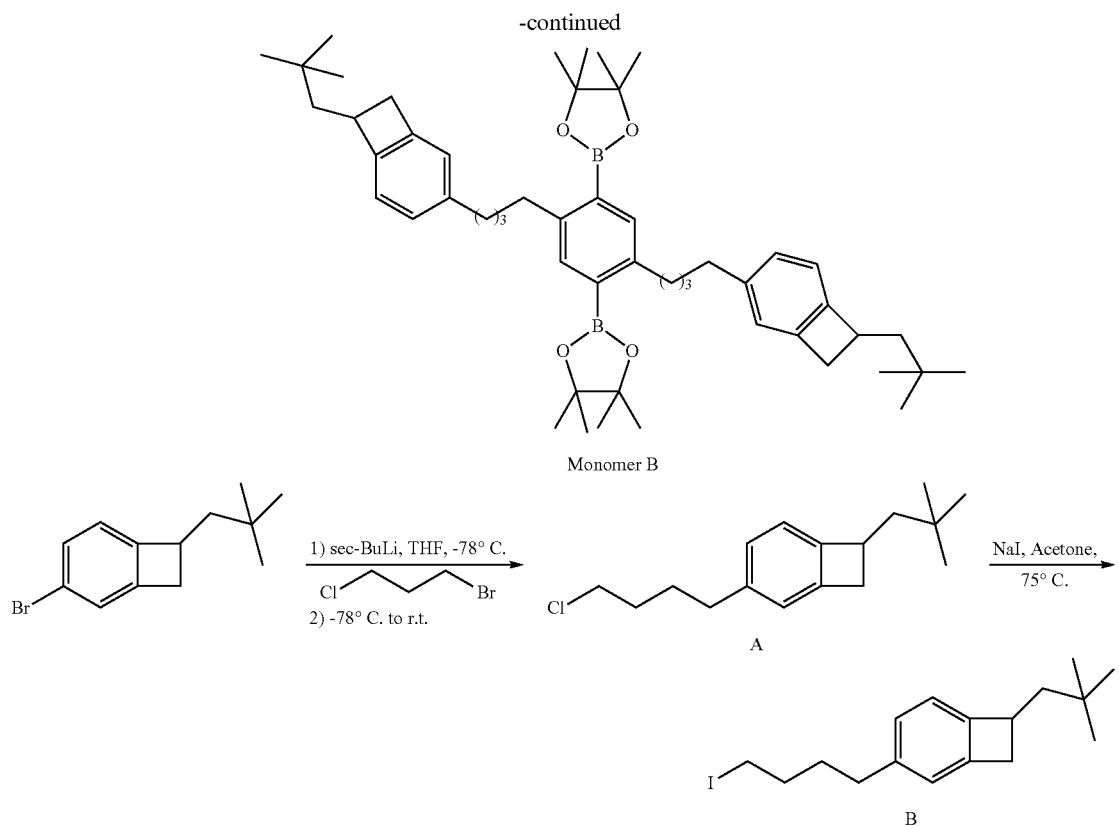

Monomer B 3-(4-chlorobutyl)-7-neopentylbicyclo[4.2.0]octa-1,3,5-triene (A)

To a solution of 3-bromo-7-neopentylbicyclo[4.2.0]octa-1,3,5-triene (33.7 g, 123.8 mmol, 93% pure by GC-MS as mixture of 2 isomers) at −78° C. in dry THF (400 ml) at −78° C. under nitrogen, was added drop wise a solution of sec-butyl lithium (118 ml, 164.4 mmol, 1.4M in cyclohexane) so as to maintain an internal temperature of <−74° C. and the reaction mixture was stirred for a further 1 hr at −78° C. Then a solution of 1-bromo-4-chlorobutane (13.5 ml, 117.7 mmol) was added drop wise so as to maintain an internal temperature of <−74° C. and the mixture allowed to warm to room temperature over night. It was then cooled to 0° C., quenched by the drop wise addition of 2M HCl (100 ml) and concentrated under vacuum. The biphasic residue was extracted with hexane (3×120 ml), the combined organic extracts were washed with water (3×200 ml), dried (MgSO$_4$) and concentrated to dryness under vacuum. The resulting oil was purified using a silica plug (hexane, hexane: DCM 9:1) give 3-(4-chlorobutyl)-7-neopentylbicyclo[4.2.0]octa-1,3,5-triene as a colourless oil (28 g, 87% yield).

$^1$H-NMR (600 MHz, CDCl$_3$): δ$_H$ [ppm] 1.0 (s, 9H), 1.57 (dd, J=8.6 Hz, 13.9 Hz, 1H), 1.72-1.84 (m, 5H), 2.61 (t, J=7.6 Hz, 2H), 2.75 (dd, J=2.5 Hz, 13.9 Hz, 1H), 3.34 (dd, J=5.3 Hz, 13.9 Hz, 1H), 3.50 (m, 1H), 3.55 (t, J=6.5 Hz, 2H), 6.88 (s, 1H), 6.98 (m, 2H).

3-(4-iodobutyl)-7-neopentylbicyclo[4.2.0]octa-1,3,5-triene (B)

A mixture of 3-(4-chlorobutyl)-7-neopentylbicyclo[4.2.0]octa-1,3,5-triene (28.0 g, 105.7 mmol) and sodium iodide (79.2 g, 528.6 mmol) in acetone (300 ml) was refluxed for 25 hrs. The mixture was cooled to room temperature, water (250 ml) added and the mixture concentrated under vacuum. The biphasic residue was extracted with hexane (3×110 ml), the combined organic extracts were washed with water (5×100 ml), dried (MgSO$_4$) and concentrated under vacuum to yield 3-(4-iodobutyl)-7-neopentylbicyclo[4.2.0]octa-1,3,5-triene as a colourless oil (36.3 g, 96% yield, 95.8% HPLC purity as a mixture of 2 isomers).

$^1$H-NMR (600 MHz, CDCl$_3$): δ$_H$ [ppm] 1.0 (s, 9H), 1.57 (dd, J=8.6 Hz, 13.9 Hz, 1H), 1.71 (quint, 2H), 1.77 (dd, J=5.2 Hz, 13.9 Hz, 1H), 1.86 (quint, 2H), 2.60 (t, J=7.6 Hz, 2H), 2.75 (dd, J=2.3 Hz, 13.9 Hz, 1H), 3.20 (t, J=7.0 Hz, 2H), 3.34 (dd, J=5.2 Hz, 13.9 Hz, 1H), 3.50 (m, 1H), 6.88 (s, 1H), 6.98 (m, 2H).

Monomer B stage 1

To a solution of 1,4-dibromo-3,6-(trimethylsilyl) benzene (20.0 g, 52.6 mmol) in dry THF (200 ml) at −78° C. under nitrogen, was added drop wise a solution of sec-butyl lithium 47.8 ml, 68.4 mmol, 1.4M in cyclohexane) so as to maintain an internal temperature of <−74° C. The reaction mixture was stirred for a further 1 hr at −78° C. Then a solution of 3-(4-iodobutyl)-7-neopentylbicyclo[4.2.0]octa-1,3,5-triene (19.7 g, 55.2 mmol) in THF (20 ml) was added drop wise while maintaining the internal temperature of <−74° C. and the mixture was allowed to warm to room temperature over night. It was then cooled to 0° C., quenched by the drop wise addition of 2M HCl (50 ml), concentrated under vacuum, and the biphasic residue was extracted with hexane (3×70 ml). The combined organic extracts were washed with water (3×100 ml), dried (MgSO$_4$) and concentrated under vacuum. The resulting oil was purified using a silica plug (hexane) yield Monomer B stage 1 as colourless oil (18.2 g, 65% yield, 85.8% HPLC purity as a mixture of 2 isomers).

$^1$H-NMR (600 MHz, CDCl$_3$): δ$_H$ [ppm] 0.29 (s, 9H), 0.38 (s, 9H), 1.0 (s, 9H), 1.53-16.3 (m, 3H), 1.71 (quint, 2H), 1.76 (dd, J=5.3 Hz, 13.9 Hz, 1H), 2.63 (m, 4H), 2.74 (dd, J=2.3 Hz, 13.9 Hz, 1H), 3.33 (dd, J=5.2 Hz, 13.9 Hz, 1H), 3.50 (m, 1H), 6.89 (s, 1H), 6.96 (d, J=7.5 Hz, 1H), 7.00 (d, J=7.5 Hz, 1H), 7.20 (s, 1H), 7.35 (s, 1H).

Monomer B stage 2

To a solution of Monomer B stage 1 (18.2 g, 34.4 mmol) in dry THF (200 ml) at −78° C. under nitrogen, was added drop wise a solution of sec-butyl lithium (29.4 ml, 41.2 mmol, 1.4M in cyclohexane) so as to maintain an internal temperature of <−74° C. and the reaction mixture was stirred for a further 1 hr at −78° C. Then a solution of 3-(4-iodobutyl)-7-neopentylbicyclo[4.2.0]octa-1,3,5-triene (12.9 g, 36.1 mmol) in THF (20 ml) was added drop wise while maintaining the internal temperature of <−74° C. and the mixture was allowed to warm to room temperature over night. It was then cooled to 0° C., quenched by the drop wise addition of 2M HCl (25 ml), concentrated under vacuum and diluted with toluene (100 ml). The phases were separated and the aqueous layer was diluted with water (50 ml) and extracted with toluene (2×50 ml). The combined organic extracts were washed with water (3×100 ml), dried (MgSO$_4$) and concentrated under vacuum. The resulting solid was stirred in acetonitrile (250 ml) for 3 hrs, filtered and dried in a vacuum oven at 40° C. for 68 hrs to yield Monomer B stage 2 as white solid (17.8 g, 76% yield, 95.5% HPLC purity).

$^1$H-NMR (600 MHz, CDCl$_3$): δ$_H$ [ppm] 0.28 (s, 18H), 1.0 (s, 18H), 1.56 (dd, J=8.7 Hz, 13.9 Hz, 2H), 1.63 (m, 4H), 1.72 (m, 4H), 1.76 (dd, J=5.3 Hz, 13.9 Hz, 2H), 2.63 (t, J=7.5 Hz, 4H), 2.67 (m, 4H), 2.75 (dd, J=2.0 Hz, 13.9 Hz, 2H), 3.33 (dd, J=5.2 Hz, 13.9 Hz, 2H), 3.49 (m, 2H), 6.89 (s, 2H), 6.96 (d, J=7.5 Hz, 2H), 7.00 (d, J=7.5 Hz, 2H), 7.35 (s, 2H).

Monomer B Stage 3

To a solution of Monomer B stage 2 (17.8 g, 26.2 mmol) in chloroform (180 ml) at 5° C. under nitrogen, shielded from light, was added drop wise acetic acid (32 ml) followed by DMF (71 ml) so as to maintain the temperature <10° C. The mixture was allowed to warm to room temperature and purged with nitrogen for 30 mins. A solution of N-bromosuccinimide (9.6 g, 53.7 mmol) in DMF (33 ml) which had been purged with nitrogen for 30 mins was added drop wise at 5° C. to the solution of Monomer B Stage 2 and the resulting mixture was allowed to warm up to room temperature and stirred for a further 3 hrs. A further portion of N-bromosuccinimide (0.4 g, 2.25 mmol) was added as a solid at 5° C. and the reaction stirred at room temperature over night. The mixture was cooled down to 10° C., water (170 ml) was added to the reaction mixture, the phases were separated, the aqueous layer was extracted with DCM (2×100 ml), the combined organic extracts were washed with water (5×100 ml) dried (MgSO$_4$) and concentrated under vacuum. The resulting solid was stirred in acetonitrile (250 ml) for 3 hrs, filtered and dried in a vacuum oven at 50° C. for 18 hours to yield Monomer B stage 3 as white solid (16.7 g, 92% yield, 95.6% pure by HPLC).

$^1$H-NMR (600 MHz, CDCl$_3$): δ$_H$ [ppm] 0.99 (s, 18H), 1.57 (dd, J=8.6 Hz, 13.9 Hz, 2H), 1.65 (m, 8H), 1.77 (dd, J=5.3 Hz, 13.9 Hz, 2H), 2.61 (t, J=7.4 Hz, 4H), 2.67 (t, J=7.4 Hz, 4H), 2.75 (dd, J=2.3 Hz, 13.9 Hz, 2H), 3.34 (dd, J=5.2 Hz, 13.9 Hz, 2H), 3.50 (m, 2H), 6.88 (s, 2H), 6.96 (d, J=7.4 Hz, 2H), 7.00 (d, J=7.5 Hz, 2H), 7.33 (s, 2H).

Monomer B

A solution of Monomer B stage 3 (16.7 g, 24.1 mmol) and bis(pinacolato)diboron (13.5 g, 53.0 mmol) in 1,2-dimethoxy ethane (200 ml) was purged with nitrogen for 1 hr, potassium acetate (14.2 g, 144.7 mmol) was added the mixture purged for a further mins. 1,1'-Bis(diphenylphosphino) ferrocene palladium dichloride dichloromethane adduct (0.59 g, 0.72 mmol) was added and the mixture stirred at 100° C. over night. The mixture was cooled down to room temperature, filtered through a silica-Florisil-celite plug (DCM:hexane (1:1)) and concentrated under vacuum. The resulting residue was dissolved in DCM and hexane was added and the DCM was removed under vacuum to obtain a mixture of DCM:hexane (1:1). The solution was filtered through a silica-Forisil plug (DCM:hexane (1:1)), and concentrated to dryness under educed pressure. The resulting solid was recrystallised repeatedly from toluene: acetonitrile, toluene:hexane and toluene:acetonitrile: isopropanol and then purified by column chromatography (hexane:DCM (7:3) to (6:4)) and the resulting solid was dissolved in toluene, acetonitrile was added to the mixture and the resulting slurry was filtered to give Monomer B as white solid (9.6 g, 50% yield, 99.8% pure by HPLC).

$^1$H-NMR (600 MHz, CDCl$_3$): δ$_H$ [ppm] 0.99 (s, 18H), 1.31 (s, 24H), 1.58 (m, 6H), 1.66 (quint, 4H), 1.76 (dd, J=5.3 Hz, 13.9 Hz, 2H), 2.59 (t, J=7.7 Hz, 4H), 2.74 (dd, J=2.0 Hz, 13.9 Hz, 2H), 2.84 (t, J=7.9 Hz, 4H), 3.32 (dd, J=5.2 Hz, 13.9 Hz, 2H), 3.48 (m, 2H), 6.87 (s, 2H), 6.94 (d, J=7.5 Hz, 2H), 6.99 (d, J=7.5 Hz, 2H), 7.53 (s, 2H).

Monomer C

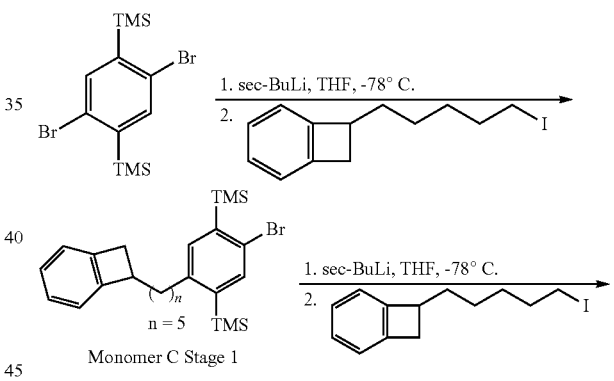

Monomer C Stage 1

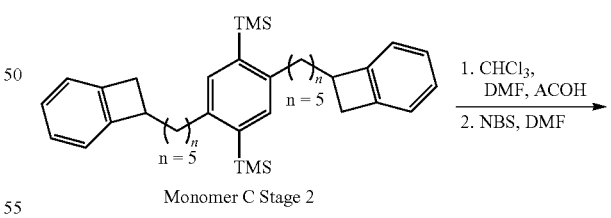

Monomer C Stage 2

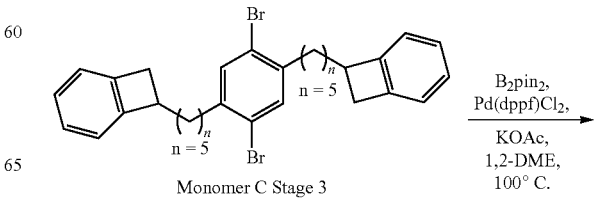

Monomer C Stage 3

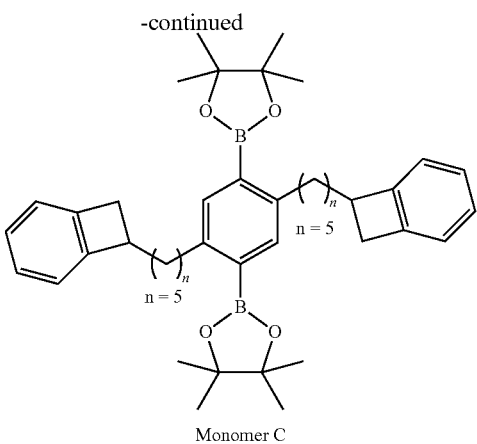

Monomer C

Monomer C Stage 1

To a solution of 1,4-dibromo-3,6-(trimethylsilyl) benzene (24.1 g, 63.4 mmol) in dry THF (200 ml) at −78° C. under nitrogen, was added drop wise a solution of s-butyl lithium (1.4M in cyclohexane, 54.4 ml, 76.1 mmol) so as to maintain an internal temperature of <−74° C. and the reaction mixture was stirred for a further 1 hr at this temperature. Then a solution of 6-(1-iodopent-5-yl)-bicyclo[4.2.0]octa-1,3,5-triene) (25 g, 66.6 mmol, 80% purity) in THF (200 ml) was added drop wise while maintaining the internal temperature of <−74° C. and the mixture allowed to warm to room temperature over night. It was then cooled to 5° C. and quenched by the drop wise addition of 2M HCl, the solvent was removed under reduced pressure, the resulting red solution was extracted with DCM (3×150 ml), the combined organic extracts were washed with water (2×250 ml) dried over MgSO$_4$ and concentrated under vacuum to give the desired product as a red oil. Purification using a silica Florisil plug (hexane) gave Monomer C stage 1 (14.4 g, 38% yield, 80% HPLC purity).

$^1$H-NMR (600 MHz, CDCl$_3$): $\delta_H$ [ppm] 0.32 (s, 9H), 0.39 (s, 9H), 1.44-1.54 (4H), 1.61 (m, 2H), 1.72 (m, 2H), 2.66 (m, 2H), 2.74 (dd, J=2.2 Hz, 13.9 Hz, 1H), 3.33 (dd, J=5.2 Hz, 13.9 Hz, 1H), 3.47 (m, 1H), 7.07 (m, 2H), 7.19 (m, 2H), 7.24 (s, 1H), 7.56 (s, 1H)

Monomer C Stage 2

To a solution of Monomer C stage 1 (14.35 g, 24.2 mmol 80% HPLC purity) in dry THF (150 ml) at −78° C. under nitrogen, was added drop wise a solution of sec-butyl lithium (1.4M in cyclohexane, 20.8 ml, 29.1 mmol) so as to maintain an internal temperature of <−74° C. and the reaction mixture was stirred for a further 1 hr at this temperature. Then a solution of 6-(1-iodopent-5-yl)-bicyclo[4.2.0]octa-1,3,5-triene) (9.54 g, 25.4 mmol, 80% HPLC pure) in THF (100 ml) was added drop wise while maintaining the internal temperature of <−74° C. and the mixture allowed to warm to room temperature over night. It was then cooled to 5° C. and quenched by the drop wise addition of HCl (2M, 100 ml) the solvent was removed under reduced pressure, the resulting solution was extracted with DCM (3×150 ml), the combined organic extracts were washed with water (2×250 ml) dried (MgSO$_4$) and concentrated to dryness under vacuum to give the desired product as a red oil. Purification using a silica Florisil plug (hexane and 10% DCM:hexane) gave Monomer C stage 2 as a clear oil (8.25 g, 48% yield, 80% HPLC purity).

$^1$H-NMR (600 MHz, CDCl$_3$): $\delta_H$ [ppm] 0.34 (s, 18H), 1.47-1.62 (8H), 1.65 (m, 4H), 1.75 (m, 4H), 2.70 (brt, 4H), 2.76 (d, J=13.9 Hz, 2H), 3.34 (dd, J=5.1 Hz, 13.9 Hz, 2H), 3.49 (m, 2H), 7.09 (m, 4H), 7.20 (quint, 4H), 7.31 (s, 2H)

Monomer C Stage 3

To a solution of Monomer C stage 2 (8.25 g, 11.64 mmol, ~80% HPLC purity) in CHCl$_3$ (80 ml) at −0° C. under nitrogen, shielded from light, was added drop wise DMF (33 ml) followed by AcOH (15 ml) so as to maintain the temperature <10° C. and the mixture allowed to warm to room temperature. A solution of NBS (4.25 g, 29.8 mmol) in DMF (17 ml) was added drop wise so as to maintain the temperature <26° C. and the mixture allowed to stir at room temperature over night. A further portion of NBS (0.5 g, 2.8 mmol) in DMF (2 ml) was added drop wise and the reaction stirred at room temperature for a further 5 hrs. Water (80 ml) was added to the reaction mixture and it was extracted with DCM (3×60 ml), the combined organic extracts were washed with water (3×100 ml) dried (MgSO$_4$) and concentrated to under vacuum to give an orange oil.

The above procedure was repeated with a further portion of NBS (2.65 g, 14.89 mmol) in DMF (8 ml) and the resulting oil was purified using a silica Florisil plug (20% DCM:hexane) to give Monomer C stage 3 as a clear oil (7.95 g, 88% yield, 75% pure by HPLC).

$^1$H-NMR (600 MHz, CDCl$_3$): $\delta_H$ [ppm] 1.45 (m, 4H), 1.48-1.59 (4H), 1.63 (quint, 4H), 1.72 (m, 4H), 2.67 (brt, 4H), 2.74 (dd, J=2.2 Hz, 13.9 Hz, 2H), 3.32 (dd, J=5.3 Hz, 13.9 Hz, 2H), 3.45 (m, 2H), 7.07 (m, 4H), 7.18 (quint, 4H), 7.40 (s, 2H)

Monomer C

A solution of Monomer C stage 3 (7 g, 9.04 mmol, ~75% HPLC purity) and bis(pinacolato)diboron (6.75 g, 26.5 mmol) 1,2-dimethoxy ethane DME (100 ml) was purged with nitrogen for 1 hr, potassium acetate (7.1 g, 72.4 mmol) was added the mixture purged with nitrogen for a further 20 mins, 1,1'-Bis(diphenylphosphino) ferrocene palladium dichloride dichloromethane adduct (0.3 g, 0.363 mmol) was added and the mixture stirred at 100° C. over night. The dark brown solution was cooled to room temperature, filtered through a Florisil-silica-celite plug (DCM:Hexane (1:1)) and concentrated to dryness. The resulting brown oil was filtered through another plug (silica-Florisil (DCM:Hexane 1:1)), to give a clear oil which solidified on standing. The resulting solid was recrystallised repeatedly from toluene: acetonitrile to give Monomer C as a white solid (1.13 g, 19% yield, 99.4% HPLC purity)

$^1$H-NMR (600 MHz, CDCl$_3$): $\delta_H$ [ppm] 1.33 (s, 24H), 1.44 (m, 4H), 1.46-1.60 (m, 8H), 1.70 (m, 4H), 2.73 (dd, J=2.1 Hz, 13.9 Hz, 2H), 2.83 (brt, 4H), 3.30 (dd, J=5.2 Hz, 13.9 Hz, 2H), 3.45 (m, 2H), 7.05 (brt, 4H), 7.17 (quint, 4H), 7.51 (s, 2H)

Monomer E

Monomer E was prepared according to the following reaction scheme:

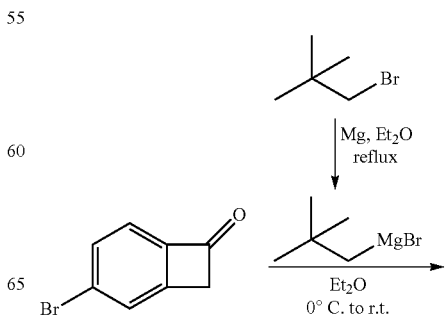

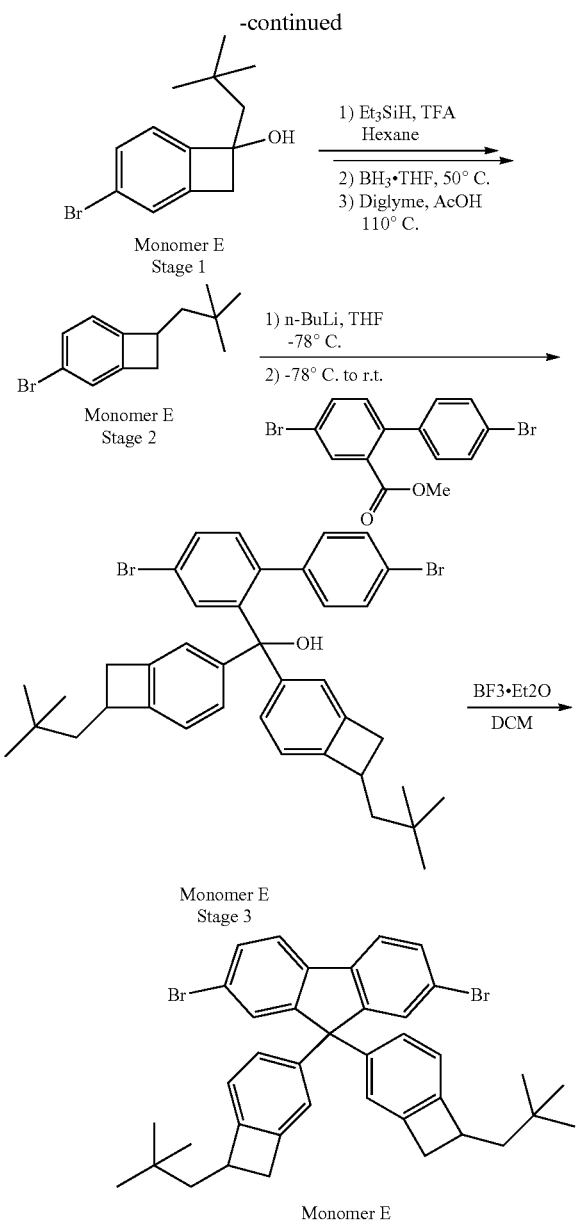

Monomer E Stage 1

To a suspension of magnesium turnings (15.42 g, 634 mmol) and iodine (3 pellets) in dry diethyl ether (10 ml) at room temperature under nitrogen, was added a solution of neopentyl bromide (77 ml, 601 mmol) in dry diethyl ether (290 ml) dropwise over 2 hr so as to maintain a gentle reflux, then the mixture was refluxed for 1 hr and then allowed to cool to room temperature. The resulting Grignard reagent was added dropwise to a solution of 3-bromobicyclo[4.2.0]octa-1,3,5-trien-7-one (100 g, 510 mmol) in dry diethyl ether (1000 ml) so as to maintain an internal temperature of ~0° C. The reaction mixture was allowed to warm to room temperature overnight, it was then cooled to 0° C., quenched with dilute hydrochloric acid (340 ml, 2M aq), and allowed to warm to room temperature. The organic phase was separated washed with water (3×120 ml), dried over MgSO$_4$ and the solvent removed under reduced pressure to give an orange oil (134 g). The oil was purified by a silica plug (eluting with hexane:ethyl acetate (95:5%)) to give the title compound as an orange oil as a mixture of two isomers (111.1 g, 0.40 mol, 78% yield, 91.8% pure by 1H NMR).

MS (EI) m/z 270 (($Br^{81}$)M$^+$, 2%), 268 (($Br^{79}$)M$^+$, 2), 255 (($Br^{81}$)M$^+$—OH, 11), 253 (($Br^{79}$)M$^+$—OH, 11), 199 (($Br^{81}$) M$^+$-neopentyl, 100), 197 (($Br^{79}$)M$^+$-neopentyl, 99)

$^1$H-NMR (600 MHz, CDCl$_3$): $\delta_H$ [ppm] 1.10 (9H, s), 1.81 (d, J=14.7 Hz, 1H), 1.94 (d, J=14.7 Hz, 1H), 3.16 (d, J=14.4 Hz, 1H), 3.48 (d, J=14.4 Hz, 1H), 7.07 (d, J=7.6 Hz, 1H), 7.29 (s, 1H), 7.37 (d, J=7.6 Hz, 1H), Monomer E Stage 2

Trifluoroacetic acid (159 ml, 2062 mmol) was added dropwise over a 1 hr period to a solution of Monomer Example 1 Stage 1 (111 g, 395 mmol) and triethylsilane (67 ml, 416 mmol) in hexane (325 ml) at 0° C. under nitrogen. The reaction was warmed to room temperature and stirred for 24 hrs. The reaction mixture was poured into a solution of ice:water (2.3 L) and stirred for 1 hr until the ice had melted and the layers had separated. The aqueous phase was extracted with hexane (500 ml), the combined organic extracts were washed with water (3×600 ml), sodium acetate (10% wt:vol, 500 ml), water (3×600 ml), dried over MgSO$_4$ and the solvent removed under reduced pressure to give an orange oil (152.7 g). The oil was purified by a silica plug (eluting with hexane) to give the title compound as a yellow oil (103.64 g, 376 mmol, 91.8% pure by $^1$H NMR (as a mixture of two isomers and containing 2% of an alkene impurity)).

A solution of the borane.THF complex (123 ml, 123 mmol) was added slowly to a solution of Monomer Example 1 Stage 2 (103.64 g, 376 mmol) in dry tetrahydrofuran (1 L) and the mixture heated to 50° C. for 18 hrs. The reaction mixture was cooled to room temperature diglyme (1.3 L) was added, the mixture cooled to 0° C. and acetic acid (610 ml) was added dropwise, (effervescence was observed). The reaction mixture was stirred overnight at room temperature and then heated to 110° C., the tetrahydrofuran was distilled off and then the mixture was heated for a further 4 hrs at 110° C., after which it was cooled to room temperature and stirred overnight. Water (200 ml) was added to the reaction mixture, it was extracted with hexane (4×1 L), the combined organic extracts were washed with water (6×1 L), dried over MgSO$_4$ and the solvent removed under reduced pressure to give the title compound as a colourless oil. The oil was purified by a silica plug (eluting with hexane) to give the title compound as a colourless oil (92.87 g, 345 mmol, 93.9% pure by $^1$H NMR as a mixture of two isomers).

MS (EI) m/z 254 (($Br^{81}$)M$^+$, 3%), 252 (($Br^{79}$)M$^+$, 2), 57 (100).

$^1$H-NMR (600 MHz, CDCl$_3$): $\delta_H$ [ppm] 0.99 (s, 9H), 1.55 (dd, J=14.0 Hz, 8.8 Hz 1H), 1.75 (dd, J=14.0 Hz, 5.2 Hz, 1H), 2.78 (dd, J=14.2 Hz, 2.5 Hz, 1H), 3.36 (dd, J=14.2 Hz, 5.2 Hz, 1H), 3.47 (dtd, J=8.8 Hz, 5.2 Hz, 2.5 Hz, 1H), 6.93 (d, J=8.0 Hz, 1H), 7.19 (s, 1H), 7.32 (d, J=8.0 Hz, 1H), Monomer E Stage 3

To a solution of Monomer Example 1 Stage 2 (7.2 g, 26.4 mmol) in dry tetrahydrofuran (70 ml) at −78° C. under nitrogen, was added dropwise a solution of n-butyl lithium (2.5M in hexane, 11.0 ml, 27.5 mmol) so as to maintain an internal temperature of <−74° C. The reaction mixture was stirred for 20 minutes and an aliquot was quenched with water and analysed by GC-MS (BCBNp/BrBCBNp 80/20). BP methyl ester (4.35 g, 11.7 mmol) was added portion wise as a solid so as to keep the internal temperature <−74° C. The mixture was allowed to warm up slowly to room temperature over night; it was then cooled to 5° C. and quenched by the drop wise addition of HCl (2M aq). The solvent was removed under reduced pressure, the residue was extracted with hexane, the combined organic extracts were washed with water, dried over MgSO$_4$ and concentrated to dryness under reduced pressure. The crude Monomer E Stage 3 was taken onto the next step without any further purification.

Monomer E

To a solution of Monomer Example 1 Stage 3 (9.19 g, 13.4 mmol) in dry dichloromethane (40 ml) at 0° C. under nitrogen, was added dropwise a solution of boron trifluoride diethyl etherate (8.23 ml, 66.9 mmol) so as to maintain an internal temperature of <5° C. The reaction mixture was allowed to warm up to room temperature, stirred over night and then poured carefully into a solution of ice:water (200 ml). Once the ice had melted, the phases were separated, the aqueous phase was extracted with dichloromethane and the combined organic extracts were stirred over an aqueous solution of potassium phosphate tribasic solution (10% wt:vol, 40 ml) for 30 minutes. The organic phase was separated and was washed with water (50 ml×3), dried over MgSO$_4$, filtered and adsorbed onto Isolute®. The dried Isolute® was loaded onto a silica/Florisil® plug and eluted with a mixture of hexane:dichloromethane (9:1 and 6:4) to give Monomer Example 1 as Frac 1 and Monomer Example 1 Stage 3 and Frac 2.

To a solution of Frac 2 (3.0 g, 4.3 mmol) in dry dichloromethane (12 ml) at 0° C. under nitrogen, was added dropwise a solution of boron trifluoride diethyl etherate (2.8 ml, 22.8 mmol) so as to maintain an internal temperature of <5° C. The reaction mixture was allowed to warm up to room temperature, stirred over night and then poured carefully into a solution of ice:water (50 ml). Once the ice had melted, phases were separated, the aqueous phase was extracted with dichloromethane and the combined organic extracts were stirred over an aqueous solution of potassium phosphate tribasic solution (10% wt:vol, 10 ml) for 30 minutes. The organic phase was separated and was washed with water (20 ml×3), dried over MgSO$_4$, filtered and adsorbed onto Isolute®. The dried Isolute® was loaded onto a silica/Florisil® plug and eluted with a mixture of hexane:dichloromethane (9:1). Fractions containing Monomer Example 1 were combined, reduced to dryness under reduced pressure and combined with Frac 1.

The resulting solid was recrystallised sequentially from n-butyl acetate:methanol followed by toluene:methanol to give Monomer E as a white solid (1.93 g, 22% yield, 100% pure by HPLC as a mixture of 2 isomers).

$^1$H-NMR (600 MHz, CDCl$_3$): δ$_H$ [ppm] 0.97 (s, 18H). 1.56 (dd, J=14.0 Hz, 8.7 Hz, 2H), 1.75 (dd, J=14.0 Hz, 5.3 Hz, 2H), 2.71 (dd, J=14.2 Hz, 2.3 Hz, 2H), 3.28 (dd, J=14.2 Hz, 5.2 Hz, 2H), 3.48 (m, 2H), 6.79 (s, 2H), 6.92 (d, J=7.8 Hz, 2H), 6.98 (dd, J=7.8 Hz, 0.96 Hz, 2H), 7.45 (dd, J=8.1 Hz, 1.6 Hz, 2H), 7.49 (d, J=1.3 Hz, 2H), 7.56 (d, J=8.1 Hz, 2H)

Polymer Examples

Polymers were prepared by Suzuki polymerisation as described in WO 00/53656 of monomers set out in Table 1.

TABLE 1

| Polymer | Diester monomers (mol %) | Dibromo monomers (mol %) |
|---|---|---|
| Comparative Polymer 1 | A (50) | D (40), G (5), Comparative Monomer 1 (5) |
| Comparative Polymer 2 | A (50) | D (40), E (5), Comparative Monomer 1 (5) |
| Polymer Example 1 | A (50) | D (40), E (5), Monomer Example 1 (5) |
| Polymer Example 2 | A (45) B (5) | D (40), F (5), Monomer Example 1 (5) |
| Polymer Example 3 | A (45) C (5) | D (40), F (5), Monomer Example 1 (5) |
| Comparative Polymer 4 | H (10), I (20), J (20) | K (27), G (10), L (3), Comparative Monomer 1 (10) |
| Polymer Example 4 | H (10), I (20), B (20) | K (27), E (10), L (3), Monomer Example 1 (10) |

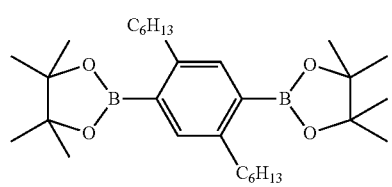

Monomer A

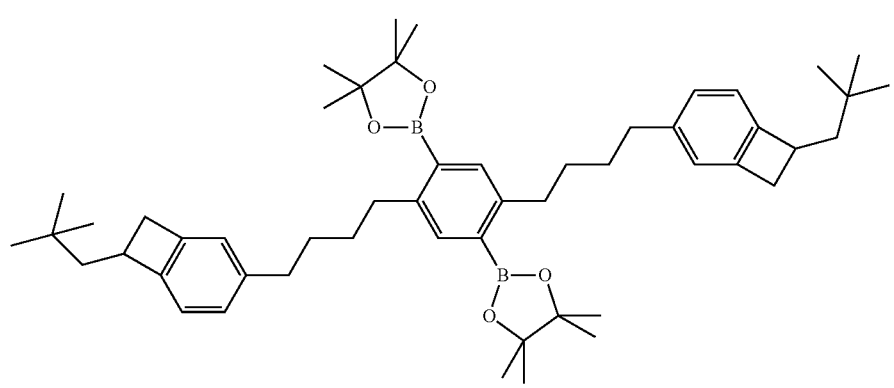

Monomer B

-continued
Monomer C
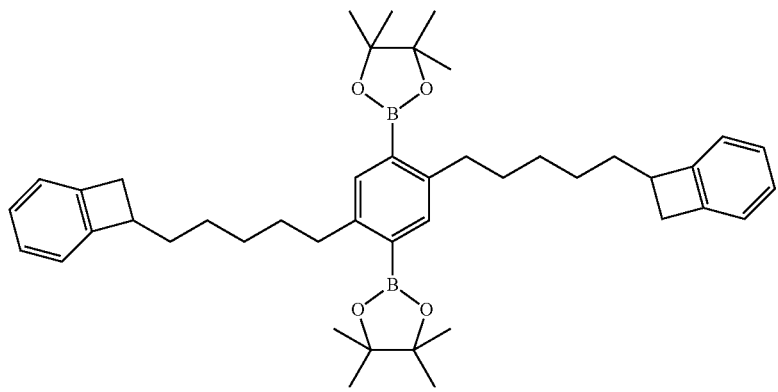
Monomer D
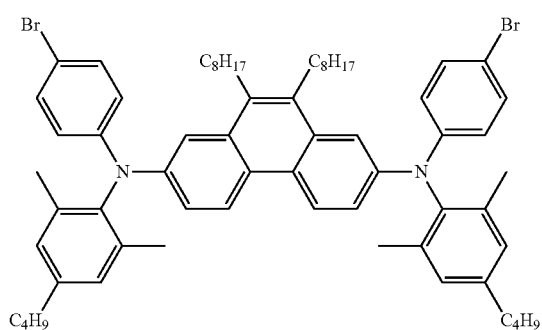
Monomer E
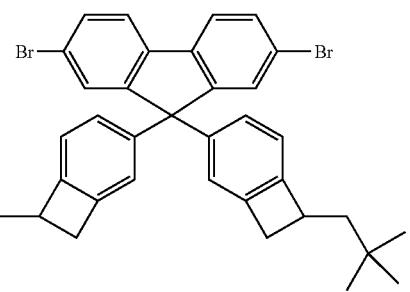
Monomer F
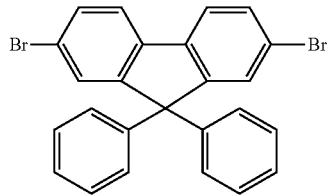
Monomer G
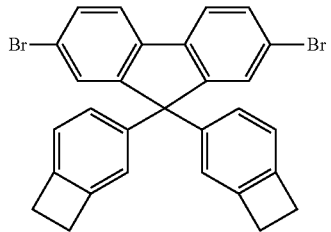
Monomer H
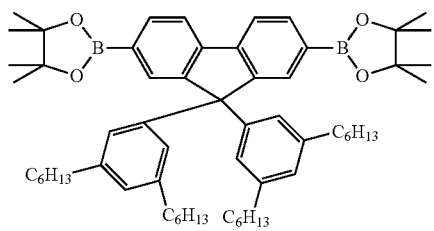
Monomer I
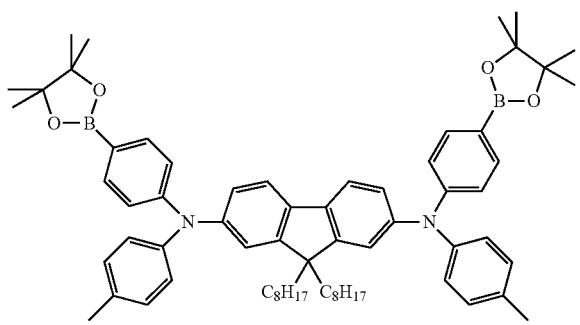

-continued
Monomer J
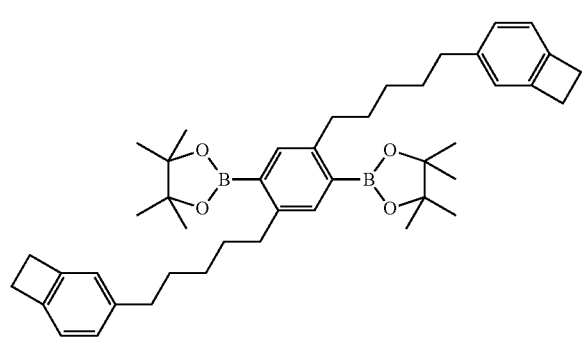
Monomer K
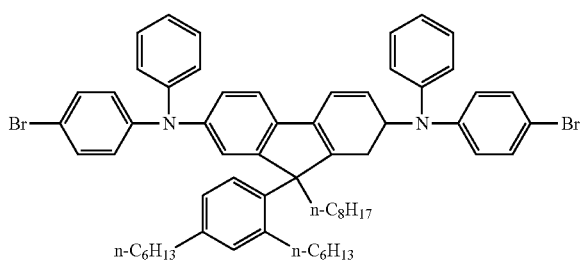
Monomer L
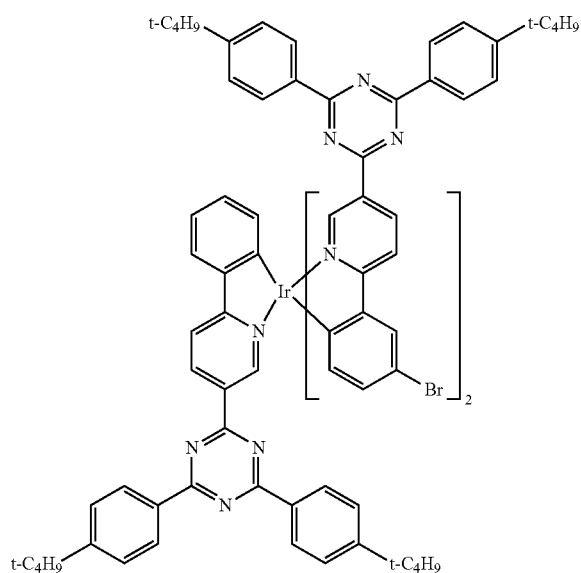
Comparative monomer 1
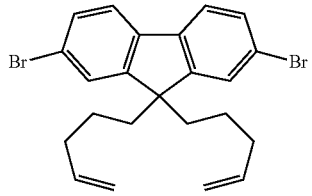
Monomer Example 1
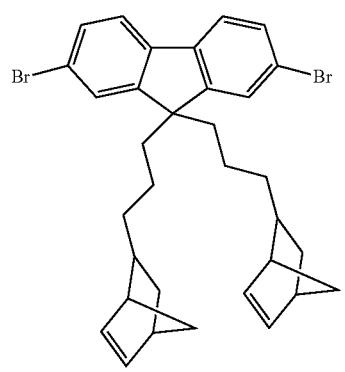

Non-polymeric Compound Reaction Example 1

17.7 mg of Compound Example 1 and 18.0 mg of BCB Compound 1, illustrated below, were weighed out into a glass disc. The glass disc was heated to 80° C. in air so both compounds were melted. The glass disc was then heated to 175° C. in a glovebox ($O_2$<0.1 ppm) and the mixture was stirred for 2 hours with a magnetic stirrer bar.

The resultant mixture was dissolved and analysed by HPLC and LC-MS, in which the peaks corresponding to the Diels Alder product were normalised to 100%.

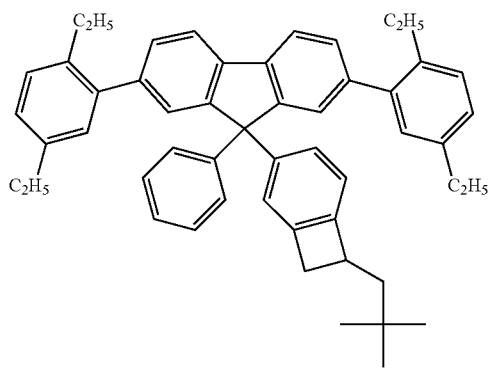 [SMILES: CCc1ccc(CC)c(-c2ccc3c(c2)C(c2ccccc2)(c2ccc4c(c2)CC4CC(C)(C)C)c2cc(-c4cc(CC)ccc4CC)ccc2-3)c1]

BCB Compound 1

Non-polymeric Compound Reaction Comparative Example 1

A reaction was performed as described in Example 1 except that 16.9 mg of Comparative Compound 1, illustrated below, was used in place of Compound Example 1.

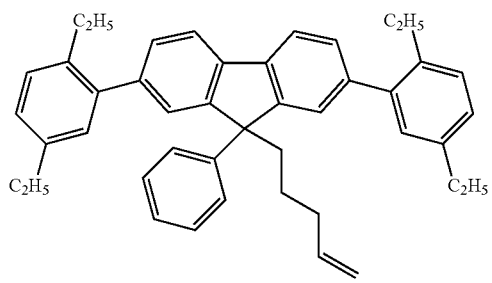 [SMILES: C=CCCCC1(c2ccccc2)c2cc(-c3cc(CC)ccc3CC)ccc2-c2ccc(-c3cc(CC)ccc3CC)cc21]

Comparative Compound 1

Figure 2:
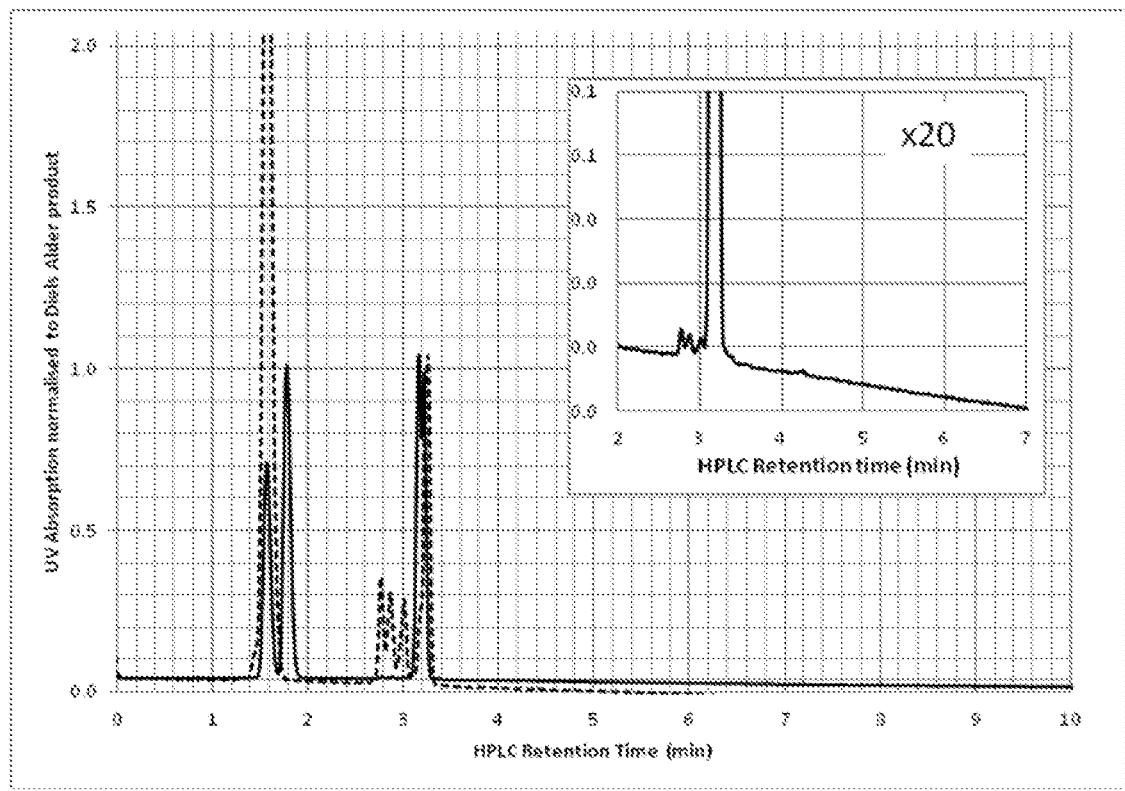
FIG. 2 shows the HPLC traces of a product mixture obtained by reaction of a composition according to an embodiment of the invention and a product mixture obtained by reaction of a comparative composition.

With reference to the HPLC traces of FIG. 2, the mixture produced by the reaction of Example 1 (solid line) contains significantly less starting material than the mixture produced by the reaction of Comparative Example 1 (dotted line). Without wishing to be bound by any theory, it is believed that this is due to a higher reactivity of Compound Example 1 compared to Comparative Compound 1.

Peaks having a retention time between about 2.5-3 minutes observed in the product mixture of Comparative Example 1 are attributed to a side-reaction in which the BCB Compound 1 reacts with itself to form a dimer. Very little such dimer formation is observed in the product mixture of Example 1. Again, without wishing to be bound by any theory it is believed that a high reactivity of Compound Example 1 makes the reaction between Compound Example 1 and BCB Compound 1 significantly more favourable than the competing dimerisation reaction of BCB Compound 1.

Polymer Reaction Examples

A 35 nm hole injection layer was formed by spin-coating a hole-injection material available from Nissan Chemical Industries on a glass substrate and annealed A 22 nm layer of a polymer of Table 1 above was formed by spin-coating on the hole-injection layer and heated to a temperature between 120° C. and 230° C. for 1 hour.

The polymer layer was then soaked in ortho-xylene solvent for 5 minutes.

The quantity of polymer that dissolved upon soaking was determined by comparing UV-vis absorption spectra at 376 nm before and after soaking in ortho xylene.

Figure 3:
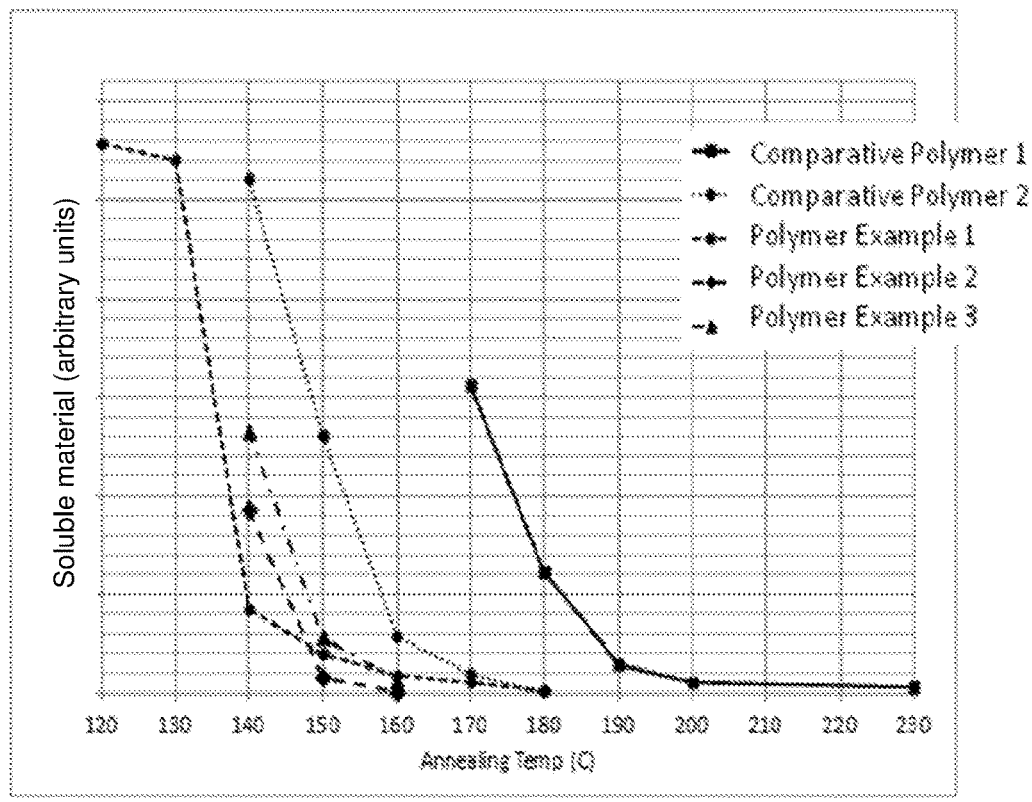
FIG. 3 is a graph of soluble material removed after heating vs. heating temperature for polymers according to embodiments of the invention and comparative polymers.

With reference to FIG. 3 crosslinking of Polymer Example 1, which contains a norbornene group, results in significantly less soluble material than crosslinking of Comparative Polymer 1 or Comparative Polymer 2 which both contain an acyclic double bond group.

Device Examples

A blue organic light-emitting device having the following structure was prepared:
ITO/HIL (35 nm)/HTL (22 nm)/LE (65 nm)/Cathode,
wherein ITO is an indium-tin oxide anode; HIL is a hole-injecting layer; HTL is a hole-transporting layer; LE is a light-emitting layer; and the cathode comprises a layer of sodium fluoride in contact with the light-emitting layer and a layer of silver and a layer of aluminium.

To form the device, a substrate carrying ITO was cleaned using UV/Ozone. The hole injection layer was formed by spin-coating an aqueous formulation of a hole-injection material available from Nissan Chemical Industries and heating the resultant layer. The hole transporting layer was formed by spin-coating a polymer of Table 1 and crosslinking the polymer by heating. The light-emitting layer was formed by spin-coating composition of a blue light-emitting polymer comprising repeat units of formulae (VII), (VIII) and (X). The cathode was formed by evaporation of a first layer of sodium fluoride to a thickness of about 2 nm, a second layer of aluminium to a thickness of about 100 nm and a third layer of silver to a thickness of about 100 nm.

The hole-transporting layers were annealed at 160° C. for 1 hour, except for Comparative Polymer 2 which was annealed at 170° C. for 1 hour.

Figure 4:
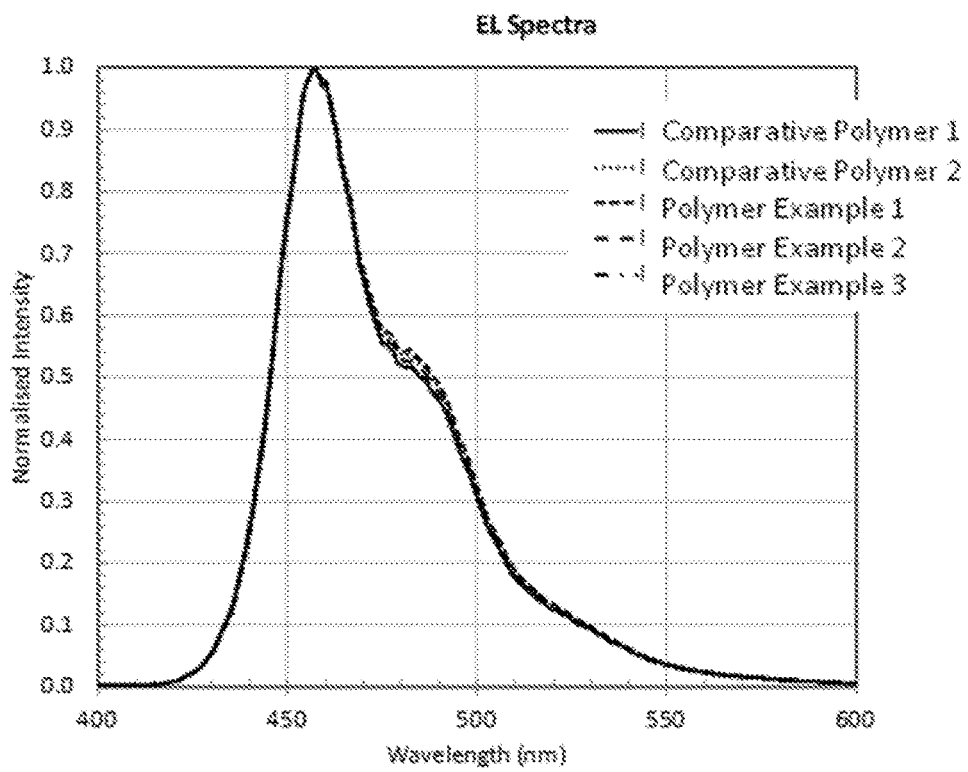
FIG. 4 shows the electroluminescence spectra for devices according to embodiments of the invention and comparative devices.

With reference to FIG. 4, the spectra using different hole-transporting layers are very similar.

Figure 5:
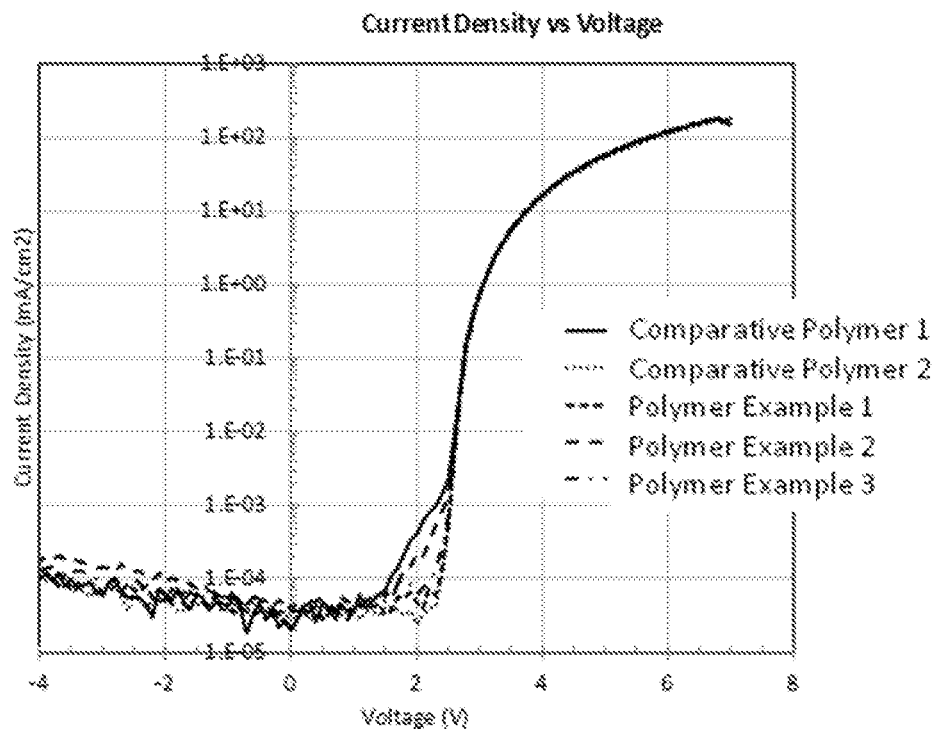
FIG. 5 shows graphs of current density vs. voltage for devices according to embodiments of the invention and comparative devices.

With reference to FIG. 5, current density at a given voltage is similar for the different devices. The voltage required to achieve a current density of 10 mA/cm$^2$ was 3.7 V in all cases.

Figure 6:
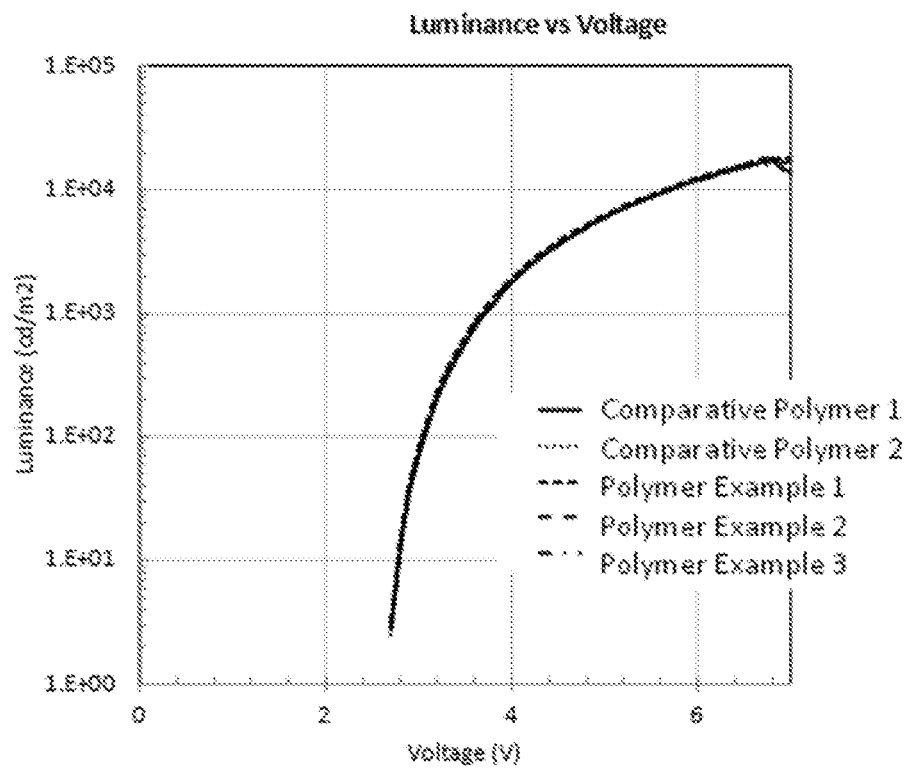
FIG. 6 shows luminance vs. voltage graphs for devices according to embodiments of the invention and comparative devices.

With reference to FIG. 6, luminance vs. voltage traces for the devices are very similar. The voltage required to achieve a brightness of 1000 cd/m$^2$ was 3.7 V in all cases.

Figure 7:
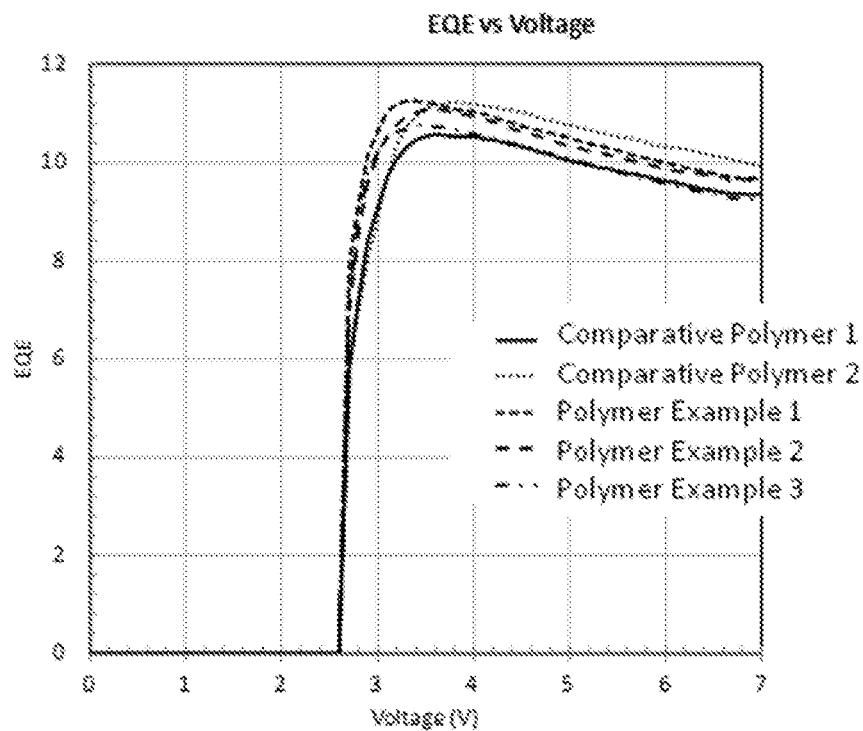
FIG. 7 shows external quantum efficiency vs. voltage graphs for devices according to embodiments of the invention and comparative devices.

With reference to FIG. 7, the external quantum efficiencies of devices containing Polymer Example 1, 2 or 3 is higher than that of devices containing Comparative Polymer 1 or 2.

Tn lifetimes of devices are provided in Table 2 wherein Tn is the time taken for lifetime to fall to n % of an initial luminance under constant current.

TABLE 2

| Hole-transporting layer polymer | T95% (hrs) | T90% (hrs) | T80% (hrs) |
|---|---|---|---|
| Comparative Polymer 1 | 15.1 | 59.9 | 269.4 |

TABLE 2-continued

| Hole-transporting layer polymer | T95% (hrs) | T90% (hrs) | T80% (hrs) |
|---|---|---|---|
| Comparative Polymer 2 | 10.9 | 45.0 | 228.5 |
| Polymer Example 1 | 12.2 | 49.8 | 244.5 |
| Polymer Example 2 | 12.5 | 51.1 | 256.6 |
| Polymer Example 3 | 13.7 | 58.5 | 285.8 |

The T95, T90 and T80 lifetimes of the device containing Polymer Example 1 containing a norbornene crosslinking repeat unit is longer than that of the device containing Comparative Polymer 2 in which the norbornene group of Polymer Example 1 is replaced with an acyclic double bond group.

White Device Examples

White organic light-emitting devices having the following structure were prepared:

ITO/HIL/LE (R)/LE (G, B)/ETL/Cathode, wherein ITO is an indium-tin oxide anode; HIL is a hole-injecting layer; LE (R) is a red light-emitting layer; LE (G, B) is a green and blue light-emitting layer; ETL is a electron-transporting layer; and the cathode comprises a layer of sodium fluoride in contact with the light-emitting layer, a layer of aluminium and a layer of silver.

To form the device, a substrate carrying ITO was cleaned using UV/Ozone. The hole injection layer was formed by spin-coating an aqueous formulation of a hole-injection material ND3202 available from Nissan Chemical Industries to a thickness of about 35 nm and heating the resultant layer. The red light-emitting layer was formed by spin-coating a polymer of Table 3 to a thickness of about 20 nm and crosslinking the polymer by heating to a temperature given in Table 3. The green and blue light-emitting layer was formed by spin-coating a composition of Host 1, Green Phosphorescent Emitter 1 and Blue Phosphorescent Emitter 1 to a thickness of about 75 nm. The electron-transporting layer was formed by spin-coating a polymer comprising the cesium salt of electron-transporting unit 1 as described in WO 2012/133229 to a thickness of 10 nm. The cathode was formed by evaporation of a first layer of sodium fluoride to a thickness of about 2 nm, a second layer of aluminium to a thickness of about 100 nm and a third layer of silver to a thickness of about 100 nm.

TABLE 3

| Device | Polymer | Heat treatment temperature (° C.) |
|---|---|---|
| Comparative Device 4A | Comparative Polymer 4 | 150 |
| Comparative Device 4B | Comparative Polymer 4 | 180 |
| Device Example 4 | Polymer Example 4 | 150 |

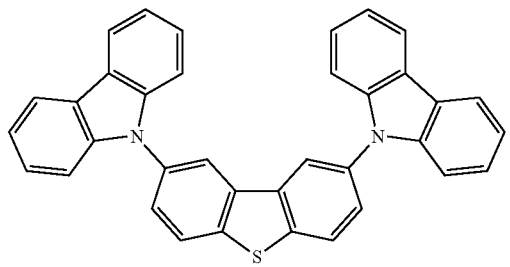 [SMILES: c1ccc2c(c1)c1ccccc1n2-c1ccc2sc3ccc(-n4c5ccccc5c5ccccc54)cc3c2c1]

TABLE 3-continued

| Device | Polymer | Heat treatment temperature (° C.) |
|---|---|---|

Host 1

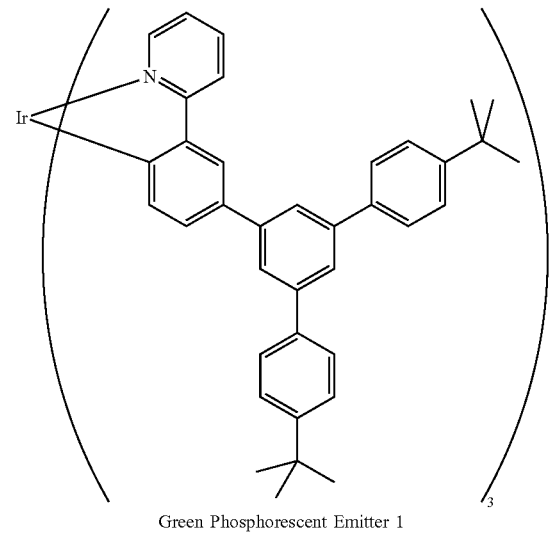

Green Phosphorescent Emitter 1

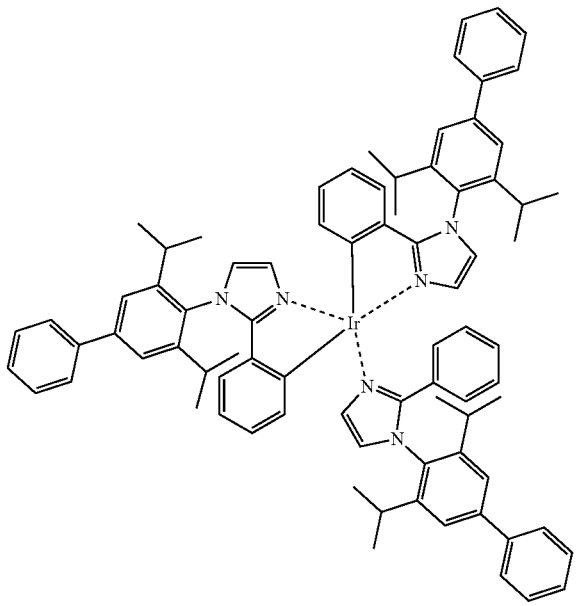

Blue Phosphorescent Emitter 1

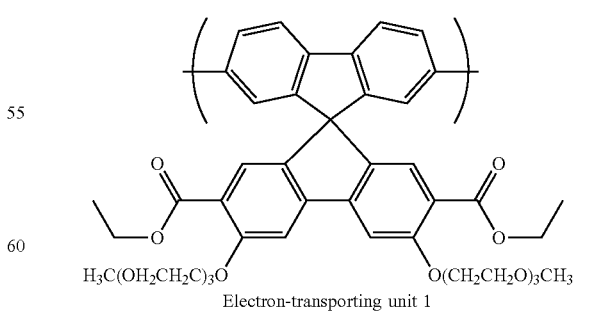

Electron-transporting unit 1

Figure 8:
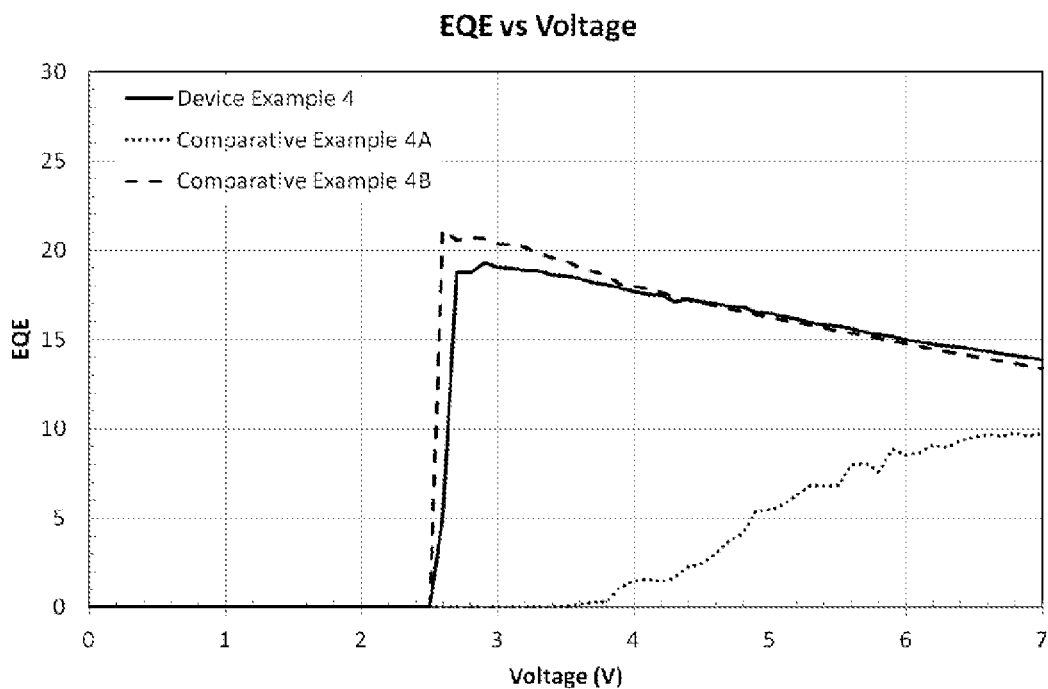
FIG. 8 is a graph of voltage vs. external quantum efficiency for a white device according to an embodiment of the invention and comparative devices.
Figure 9:
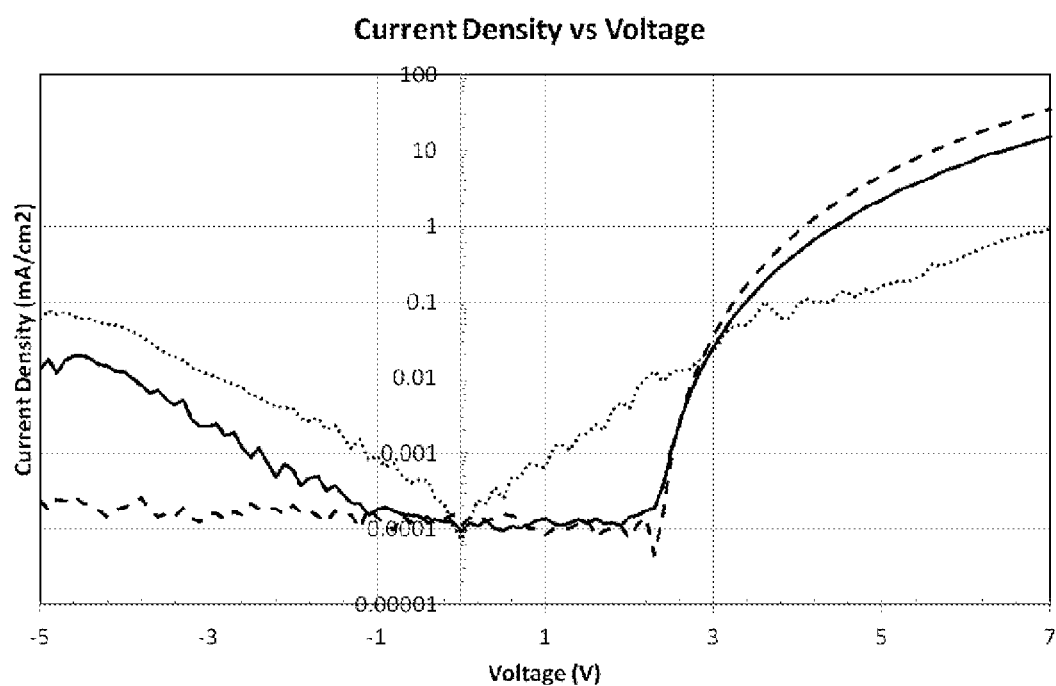
FIG. 9 is a graph of current density vs. voltage for a white device according to an embodiment of the invention and comparative devices.

With reference to FIGS. 8 and 9, the external quantum efficiency and current density of Device Example 4A is much worse than that of Device Example 4. Efficiency and current density comparable to that of Device Example 4 is only achieved by heating Comparative Polymer 4 at a significantly higher temperature.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A composition comprising a first material substituted with at least one group of formula (I) and a second material substituted with at least one group selected from groups of formulae (IIa) and (IIb):

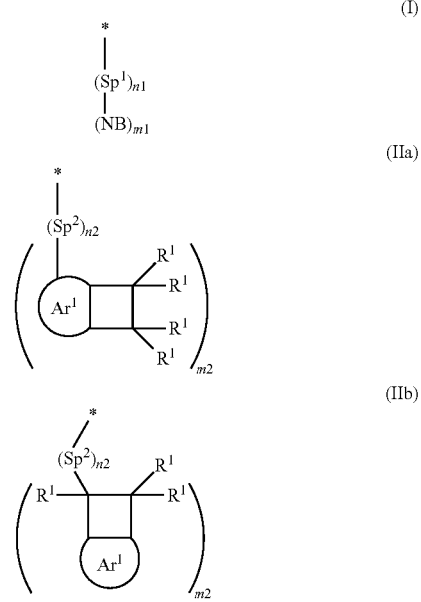

wherein at least one of the first material and the second material is a repeat unit of a polymer;

wherein:

Sp$^1$ represents a first spacer group;

NB independently in each occurrence is a norbornene group that may be unsubstituted or substituted with one or more substituents;

n1 is 0 or 1;

m1 is 1 if n1 is 0 and m1 is at least 1 if n1 is 1;

Sp$^2$ represents a second spacer group;

n2 is 0 or 1;

m2 is 1 if n2 is 0 and m2 is at least 1 if n2 is 1;

Ar$^1$ independently in each occurrence represents an aryl or heteroaryl group that may be unsubstituted or substituted with one or more substituents;

R$^1$ independently in each occurrence is H or a substituent; and

\* represents a point of attachment to the first or second material.

2. The composition according to claim 1 wherein the substituent of formula (I) has formula (Ia):

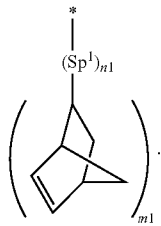

3. The composition according to claim 1 wherein n1 is 1 and Sp$^1$ is a C$_{1-20}$ alkyl group.

4. The composition according to claim 1 wherein n2 is 1 and Sp$^2$ is a C$_{1-20}$ alkyl group.

5. The composition according to claim 1 wherein at least one R$^1$ is not H.

6. The composition according to claim 1 wherein Ar$^1$ is unsubstituted or substituted phenyl.

7. The composition according to claim 1 wherein at least one of the first and second materials is a non-polymeric material.

8. The composition according to claim 1 wherein the first material is a first repeat unit of formula (IIIc):

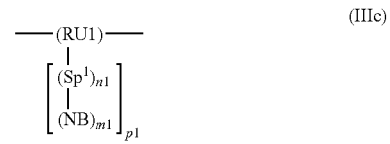

wherein RU1 is a first polymer backbone repeating group and p1 is at least 1.

9. The composition according to claim 8 wherein RU1 is an unsubstituted or substituted arylene group.

10. The composition according to claim 1 wherein the second material is a second repeat unit of formula (IVc) or (IVd):

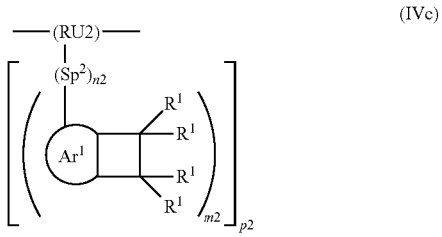

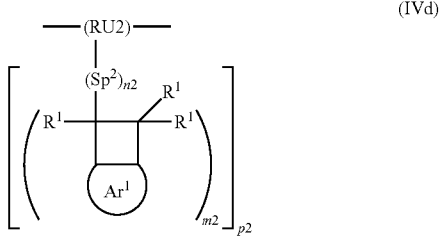

wherein RU2 is a second polymer backbone repeating group and p2 is at least 1.

11. The composition according to claim 10 wherein RU2 is an unsubstituted or substituted arylene group.

12. The composition according to claim 1 wherein the first and second materials are first and second repeat units of the same polymer.

13. A method of forming a layer of an organic electronic device comprising the step of reacting a composition comprising a first material substituted with at least one group of formula (I) and a second material substituted with at least one group selected from groups of formulae (IIa) and (IIb):

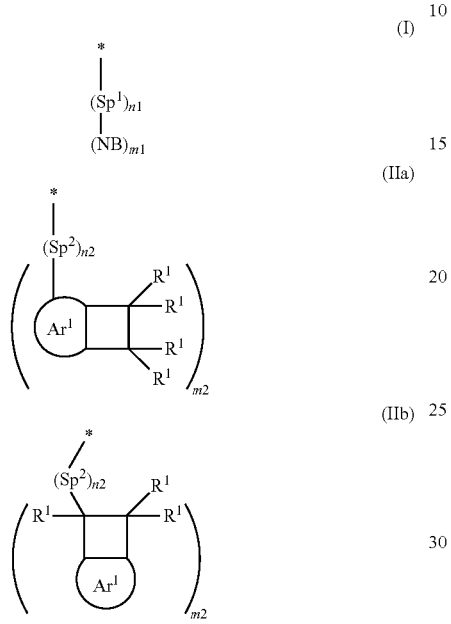

wherein at least one of the first material and the second material is a repeat unit of a polymer;
wherein:
Sp$^1$ represents a first spacer group;
NB independently in each occurrence is a norbornene group that may be unsubstituted or substituted with one or more substituents;
n1 is 0 or 1;
m1 is 1 if n1 is 0 and m1 is at least 1 if n1 is 1;
Sp$^2$ represents a second spacer group;
n2 is 0 or 1;
m2 is 1 if n2 is 0 and m2 is at least 1 if n2 is 1;
Ar$^1$ independently in each occurrence represents an aryl or heteroaryl group that may be unsubstituted or substituted with one or more substituents;
R$^1$ independently in each occurrence is H or a substituent; and
\* represents a point of attachment to the first or second material.

14. The method according to claim 13 wherein the reaction takes place at a temperature less than 200° C.

15. The method according to claim 13 wherein the organic electronic device is an organic light-emitting device.

16. The method according to claim 15 wherein the layer is a hole transporting layer provided between an anode and a light-emitting layer of the organic light-emitting device.

17. The method according to claim 16 wherein the light-emitting layer is formed by depositing a formulation comprising a light-emitting material and one or more solvents onto the hole transporting layer, and evaporating the one or more solvents.

18. A composition comprising a first material substituted with at least one group of formula (I) and a second material substituted with at least one group selected from groups of formulae (IIa) and (IIb):

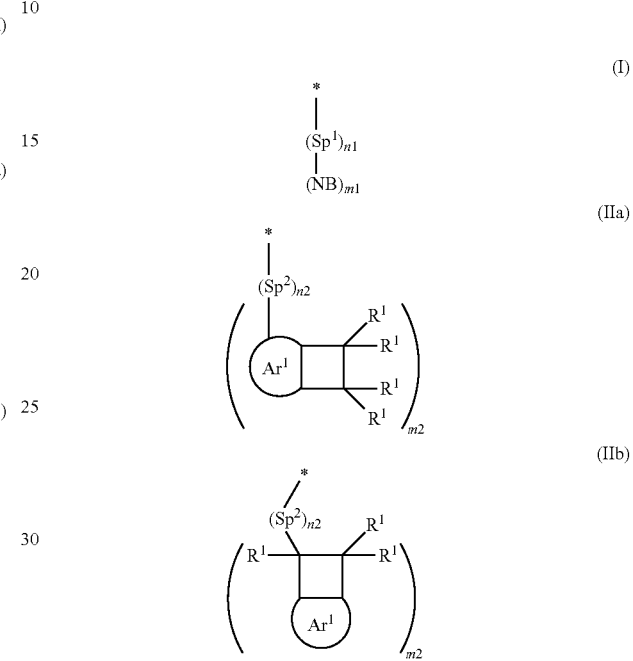

wherein:
Sp$^1$ represents a first spacer group;
NB independently in each occurrence is a norbornene group that may be unsubstituted or substituted with one or more substituents;
n1 is 0 or 1;
m1 is 1 if n1 is 0 and m1 is at least 1 if n1 is 1;
Sp$^2$ represents a second spacer group;
n2 is 0 or 1;
m2 is 1 if n2 is 0 and m2 is at least 1 if n2 is 1;
Ar$^1$ independently in each occurrence represents an aryl or heteroaryl group that may be unsubstituted or substituted with one or more substituents;
R$^1$ independently in each occurrence is H or a substituent, wherein at least one R$^1$ is not H; and
\* represents a point of attachment to the first or second material.

19. The composition according to claim 18 wherein at least one of the first and second materials is a non-polymeric material.

20. The composition according to claim 18 wherein both of the first and second materials are non-polymeric materials.

\* \* \* \* \*